United States Patent
Zwirn

(10) Patent No.: US 10,908,269 B2
(45) Date of Patent: Feb. 2, 2021

(54) CLUTTER SUPPRESSION IN ULTRASONIC IMAGING SYSTEMS

(71) Applicant: CRYSTALVIEW MEDICAL IMAGING LIMITED, St. Helier (JE)

(72) Inventor: Gil Zwirn, Petah Tikva (IL)

(73) Assignee: CRYSTALVIEW MEDICAL IMAGING LIMITED, St. Helier (JE)

( * ) Notice: Subject to any disclaimer, the term of this patent is extended or adjusted under 35 U.S.C. 154(b) by 464 days.

(21) Appl. No.: 15/555,970

(22) PCT Filed: Mar. 7, 2016

(86) PCT No.: PCT/IB2016/051273
§ 371 (c)(1),
(2) Date: Sep. 5, 2017

(87) PCT Pub. No.: WO2016/139647
PCT Pub. Date: Sep. 9, 2016

(65) Prior Publication Data
US 2018/0038947 A1 Feb. 8, 2018

Related U.S. Application Data

(60) Provisional application No. 62/128,525, filed on Mar. 5, 2015.

(51) Int. Cl.
*G03B 42/06* (2006.01)
*G01S 7/52* (2006.01)
(Continued)

(52) U.S. Cl.
CPC ........ *G01S 7/52077* (2013.01); *A61B 8/4494* (2013.01); *G01S 7/52047* (2013.01);
(Continued)

(58) Field of Classification Search
None
See application file for complete search history.

(56) References Cited

U.S. PATENT DOCUMENTS

| | | | | |
|---|---|---|---|---|
| 5,419,332 A | * | 5/1995 | Sabbah | A61B 8/06 600/455 |
| 6,068,598 A | * | 5/2000 | Pan | A61B 8/06 600/453 |

(Continued)

*Primary Examiner* — Hovhannes Baghdasaryan
*Assistant Examiner* — Jonathan D Armstrong
(74) *Attorney, Agent, or Firm* — Fresh IP PLC; Clifford D. Hyra; Aubrey Y Chen

(57) ABSTRACT

Methods of ultrasound imaging, some of which comprise: generating one or more transmit beams, wherein the boresight of each of the transmit beams points to a direction associated with a target region generating one or more receive beams using a probe (26) comprising a transducer array (30); for each receive beam or group of receive beams, sampling the received signal one or more times, wherein each sample is associated with a certain volume within the target region ("volume-gate"), and wherein multiple space-dependent samples are taken over the probe for each volume-gate; and processing the space-dependent samples, said processing comprising: applying beamforming sample alignment such that each space-dependent sample associated with a volume-gate is aligned; for each aligned volume-gate, computing one or more clutter suppression features, wherein a clutter suppression feature is dependent on the signal variability of the space-dependent samples; for each aligned volume-gate, computing a metric value wherein the metric value depends on values of one or more of the one or more clutter suppression features for the aligned volume-gate, and performing a beamforming summation step in accordance with the metric value.

16 Claims, 10 Drawing Sheets

(51) Int. Cl.
    *G01S 15/89* (2006.01)
    *A61B 8/00* (2006.01)
(52) U.S. Cl.
    CPC ...... *G01S 7/52085* (2013.01); *G01S 15/8918* (2013.01); *G01S 15/8997* (2013.01); *G01S 15/8915* (2013.01); *G01S 15/8927* (2013.01)

(56) References Cited

U.S. PATENT DOCUMENTS

| | | | | |
|---|---|---|---|---|
| 6,322,509 | B1 * | 11/2001 | Pan | A61B 5/1075 |
| | | | | 600/443 |
| 6,390,984 | B1 * | 5/2002 | Pan | A61B 8/06 |
| | | | | 600/453 |
| 8,357,094 | B2 * | 1/2013 | Mo | A61B 8/00 |
| | | | | 600/407 |
| 8,879,813 | B1 * | 11/2014 | Solanki | A61B 3/14 |
| | | | | 382/128 |
| 2004/0029213 | A1 * | 2/2004 | Callahan | G06K 9/4609 |
| | | | | 435/40.5 |
| 2006/0239553 | A1 * | 10/2006 | Florin | G06K 9/38 |
| | | | | 382/173 |
| 2007/0096975 | A1 * | 5/2007 | Maskell | G01S 13/723 |
| | | | | 342/95 |
| 2009/0129646 | A1 * | 5/2009 | Zwirn | A61B 5/0046 |
| | | | | 382/128 |
| 2010/0172567 | A1 * | 7/2010 | Prokoski | G01K 13/002 |
| | | | | 382/132 |
| 2014/0348410 | A1 * | 11/2014 | Grunkin | G06T 7/33 |
| | | | | 382/133 |
| 2018/0000456 | A1 * | 1/2018 | Wong | A61B 8/06 |
| 2019/0015059 | A1 * | 1/2019 | Itu | G06T 7/11 |
| 2020/0051246 | A1 * | 2/2020 | Carmi | G06T 11/001 |
| 2020/0257879 | A1 * | 8/2020 | Solanki | G06T 5/20 |

* cited by examiner

CLUTTER SUPPRESSION IN ULTRASONIC IMAGING SYSTEMS

RELATED APPLICATION

This application claims priority from U.S. Provisional Patent Application 62/128,525 filed Mar. 5, 2015, the content of which is hereby incorporated by reference.

FIELD OF THE INVENTION

The present invention relates generally to ultrasonic imaging systems, e.g., for medical imaging, and particularly to methods and systems for suppressing clutter effects in ultrasonic imaging systems.

BACKGROUND OF THE INVENTION

Ultrasonic medical imaging plays a crucial role in modern medicine, gradually becoming more and more important as new developments enter the market. Some of the most common ultrasound imaging applications are cardiac imaging (also referred to as echocardiography), abdominal imaging, and obstetrics and gynecology. Ultrasonic imaging is also used in various other industries, e.g., for flaw detection during hardware manufacturing.

Ultrasound images often include artifacts, making the analysis and/or diagnosis of these images a task for highly trained experts. One of the most problematic imaging artifacts is clutter, i.e., undesired information that appears in the imaging plane or volume, obstructing data of interest.

One of the main origins of clutter in ultrasonic imaging is effective imaging of objects outside the mainlobe of the probe's beam, also referred to as sidelobe clutter. Such objects may distort the signal associated with certain imaged spatial regions, adding to them signals originating from irrelevant spatial directions. In most cases, objects in the probe's sidelobes cause significant signal distortion if they are highly reflective to ultrasound waves and/or are located in spatial angles for which the probe's sidelobe level is relatively high. For example, in echocardiography, the dominant reflectors outside the probe's mainlobe are typically the ribcage and the lungs.

Another origin of clutter is multi-path reflections, also called reverberations. In some cases, the geometry of the scanned region with respect to the probe, as well as the local reflective characteristics within the scanned region, causes a noticeable percentage of the transmitted energy to bounce back and forth before reaching the probe. As a result, the signal measured for a certain range with respect to the probe may include contributions from other ranges, in addition to the desired range. If the signal emanating from other ranges is caused by highly reflective elements, it may have a significant effect on the image quality.

A common medical imaging method for enhancing the visibility of the desired ultrasonic information relative to the clutter is administering contrast agents. Such agents enhance the ultrasonic backscatter from blood and aid in its differentiation from surrounding tissues. They are used, for example, to enhance image quality in patients with low echogenicity, a common phenomenon among obese patients. This method is described, for example, by Krishna et al., in a paper entitled "Sub-harmonic Generation from Ultrasonic Contrast Agents," Physics in Medicine and Biology, vol. 44, 1999, pages 681-694.

Using harmonic imaging instead of fundamental imaging, i.e., transmitting ultrasonic signals at a certain frequency and receiving at an integer multiple, for instance 2, of the transmitted frequency, also reduces clutter effects. Spencer et al. describe this method in a paper entitled "Use of Harmonic Imaging without Echocardiographic Contrast to Improve Two-Dimensional Image Quality," American Journal of Cardiology, vol. 82, 1998, pages 794-799.

U.S. Pat. No. 6,251,074, by Averkiou et al., issued on Jun. 26, 2001, titled "Ultrasonic Tissue Harmonic Imaging," describes ultrasonic diagnostic imaging systems and methods which produce tissue harmonic ultrasonic images from harmonic echo components of a transmitted fundamental frequency. Fundamental frequency waves are transmitted by an array transducer to focus at a focal depth. As the transmitted waves penetrate the body, the harmonic effect develops as the wave components begin to focus. The harmonic response from the tissue is detected and displayed, while clutter from fundamental response is reduced by excluding fundamental frequencies.

Moreover, clutter may be reduced using a suitable probe design. U.S. Pat. No. 5,410,208, by Walters et al., issued on Apr. 25, 1995, titled "Ultrasound Transducers with Reduced Sidelobes and Method for Manufacture Thereof," discloses a transducer with tapered piezoelectric layer sides, intended to reduce sidelobe levels. In addition, matching layers disposed on the piezoelectric layer may similarly be tapered to further increase performance. Alternative to tapering the piezoelectric layer, the top electrode and/or the matching layers may be reduced in size relative to the piezoelectric layer such that they generate a wave which destructively interferes with the undesirable lateral wave.

Furthermore, image-processing methods have been developed for detecting clutter-affected pixels in echocardiographic images by means of post-processing. Zwirn and Akselrod present such a method in a paper entitled "Stationary Clutter Rejection in Echocardiography," Ultrasound in Medicine and Biology, vol. 32, 2006, pages 43-52.

Other methods utilize auxiliary receive ultrasound beams. In U.S. Pat. No. 8,045,777, issued on Oct. 25, 2011, titled "Clutter Suppression in Ultrasonic Imaging Systems," Zwirn describes a method for ultrasonic imaging, comprising: transmitting an ultrasonic radiation towards a target; receiving reflections of the ultrasonic radiation from a region of the target in a main reflected signal and one or more auxiliary reflected signals, wherein each one of the reflected signals is associated with a different and distinct beam pattern, wherein all of the reflected signals have an identical frequency; determining a de-correlation time of at least one of: the main reflected signal and the one or more auxiliary reflected signals; applying a linear combination to the main reflected signal and the one or more auxiliary reflected signals, to yield an output signal with reduced clutter, wherein the linear combination comprises a plurality of complex number weights that are being determined for each angle and for each range within the target tissue, wherein each complex number weight is selected such that each estimated reflection due to the clutter is nullified, wherein a reflection is determined as associated with clutter if the determined de-correlation time is above a specified threshold.

U.S. patent application 2012/0157851, by Zwirn, published on Jun. 21, 2012, titled "Clutter Suppression in Ultrasonic Imaging Systems," describes a method of ultrasound imaging including the following steps: transmitting ultrasound radiation towards a target and receiving reflections of the ultrasound radiation from a region of the target in a main reflected signal and one or more auxiliary reflected signals, wherein each one of the reflected signals comprises an input dataset and is associated with a different and distinct beam pattern; compounding the input datasets from the main reflected signal and one or more auxiliary reflected signals, by the use of a compounding function, said compounding function using parameters derived from spatial analysis of the input datasets.

U.S. Pat. No. 8,254,654, by Yen and Seo, issued on Aug. 28, 2012, titled "Sidelobe Suppression in Ultrasound Imaging using Dual Apodization with Cross-Correlation," describes a method of suppressing sidelobes in an ultrasound image, the method comprising: transmitting a focused ultrasound beam through a sub-aperture into a target and collecting resulting echoes; in receive, using a first apodization function to create a first dataset; in receive, using a second apodization function to create a second dataset; combining the two datasets to create combined RF data; calculating a normalized cross-correlation for each pixel; performing a thresholding operation on each correlation value; and multiplying the resulting cross-correlation matrix by the combined RF data.

Further clutter suppression methods are based on analyzing spatial and/or temporal self-similarity within the ultrasound data. G.B. patent 2,502,997, by Zwirn, issued on Sep. 3, 2014, titled "Suppression of Reverberations and/or Clutter in Ultrasonic Imaging Systems," discloses a method for clutter suppression in ultrasonic imaging, the method comprising: transmitting an ultrasonic radiation towards a target medium via a probe; receiving reflections of the ultrasonic radiation from said target medium in a reflected signal via a scanner, wherein the reflected signal is spatially arranged in a scanned data array, which may be one-, two-, or three-dimensional, so that each entry into the scanned data array corresponds to a pixel or a volume pixel (either pixel or volume pixel being collectively a "voxel"), and wherein the reflected signal may also be divided into frames, each of which corresponding to a specific timeframe (all frames being collectively a "cine-loop"); said method being characterized by the following: step 110—computing one or more self-similarity measures between two or more voxels or groups of voxels within a cine-loop or within a processed subset of the cine-loop, so as to assess their self-similarity; step 120—for at least one of: (i) each voxel; (ii) each group of adjacent voxels within the cine-loop or the processed subset of the cine-loop; and (iii) each group of voxels which are determined to be affected by clutter, based on one or more criteria, at least one of which relates to the self-similarity measures computed in step 110, computing one or more clutter parameters, at least one of which also depends on the self-similarity measures computed in step 110; and step 130—for at least one of: (i) each voxel; (ii) each group of adjacent voxels within the cine-loop or the processed subset of the cine-loop; and (iii) each group of voxels which are determined to be clutter affected voxels, based on one or more criteria, at least one of which relates to the self-similarity measures computed in step 110, applying clutter suppression using the corresponding suppression parameters.

An additional class of currently available methods for handling clutter is a family of clutter rejection algorithms, used in color-Doppler flow imaging. These methods estimate the flow velocity inside blood vessels or cardiac chambers and suppress the effect of slow-moving objects, using the assumption that the blood flow velocity is significantly higher than the motion velocity of the surrounding tissue. These methods are described, for example, by Herment et al. in a paper entitled "Improved Estimation of Low Velocities in Color Doppler Imaging by Adapting the Mean Frequency Estimator to the Clutter Rejection Filter," IEEE Transactions on Biomedical Engineering, vol. 43, 1996, pages 919-927.

SUMMARY OF THE INVENTION

Embodiments of the present invention provide methods and devices for reducing clutter effects in ultrasonic imaging systems.

According to a first aspect of the invention there is provided a method of ultrasound imaging, said method comprising generating one or more transmit beams, wherein the boresight of each of the transmit beams points to a direction associated with a target region, generating one or more receive beams using a probe (26) comprising a transducer array, for each receive beam or group of receive beams, sampling the received signal one or more times, wherein each sample is associated with a certain volume within the target region ("volume-gate"), and wherein multiple space-dependent samples are taken over the probe for each volume-gate; and processing the space-dependent samples, said processing comprising applying beamforming sample alignment such that each space-dependent sample associated with a volume-gate is aligned, for each aligned volume-gate, computing one or more clutter suppression features, wherein a clutter suppression feature is dependent on the signal variability of the space-dependent samples; for each aligned volume-gate, computing a metric value wherein the metric value depends on values of one or more of the one or more clutter suppression features for the aligned volume-gate, and performing a beamforming summation step in accordance with the metric value.

The beamforming summation step may comprise modifying the space-dependent samples associated with the aligned volume-gate in accordance with the metric value and applying beamforming summation to sum over the modified samples associated with the aligned volume gate to provide a beamformed sample value.

The beamforming summation step may comprise applying beamforming summation to sum over the space-dependent samples associated with the aligned volume-gate to provide a beamformed sample value and applying a clutter suppression function to the beamformed sample value, wherein the clutter suppression function is a function depending on the metric value for the corresponding aligned volume-gate.

The method may further comprise applying an output transfer function to the results.

The sampling may be performed either before or after applying matched filtering.

The sampling may be real or complex.

Each sample or group of samples associated with taking multiple space-dependent samples over the probe may be associated with one of a different receiving element of the transducer array; a different receiving sub-array of the transducer array; and a different phase center.

Taking multiple space-dependent samples over the probe may comprise one or more of the following: using per-channel sampling, such that each of the multiple space-dependent samples over the probe is associated with a different receiving element of the transducer array (30); sampling per sub-array, such that each of the multiple space-dependent samples over the probe is associated with a different receiving sub-array of the transducer array (30); generating two or more receive beams, each having a different phase center, applying beamforming for each such receive beam, and collecting the data associated with each volume-gate together to obtain the multiple space-dependent samples over the probe; using synthetic aperture data acquisition, wherein each transmit pulse uses a single element or a certain sub-array of the transducer array (30), and the same element or sub-array is used on reception for that pulse; using synthetic aperture data acquisition, wherein each transmit pulse employs a single element or a certain sub-array of the transducer array (30), and on reception, for each transmit pulse, a certain element or sub-array or the entire transducer array (30) is employed, wherein the set of elements used on transmission and the set of elements used on reception do not always match; and using orthogonal sub-array coded excitation, with per-channel sampling or sampling per sub-array.

The beamforming sample alignment may be associated with one of beamforming on reception only; and beamforming on both transmission and reception.

The step of applying beamforming sample alignment may further comprise applying beamforming summation, associated with beamforming on transmission.

A space-dependent sample array may be the result of arranging the space-dependent samples over the probe for a given volume-gate in an array, which may be one-dimensional, two-dimensional or multi-dimensional; and wherein at least one of the clutter suppression features is computed from one or more of:

i) the standard deviation or variance of the space-dependent sample array, taking into account one or more of the following components of the array's signal: magnitude, phase, real component, and/or imaginary component;

ii) a certain statistic (e.g., mean, median, predefined percentile) of the spatial derivatives within the space-dependent sample array, taking into account one or more of the following components of the array's signal: magnitude, phase, real component, and/or imaginary component;

iii) a feature associated with counting zero-crossings within the space-dependent sample array; wherein when the space-dependent sample array is real, a zero-crossing is defined as a sign change between adjacent array elements and/or the occurrence of a value being very close to 0; and when the space-dependent sample array is complex, a zero-crossing is defined as a local minimum of the signal magnitude;

iv) a feature associated with estimating peak widths within the space-dependent sample array, wherein the peak may be associated with one or more of the following components of the array's signal: magnitude, phase, real component, and/or imaginary component;

v) the width of the output of the auto-correlation function applied to the space-dependent sample array;

vi) a feature associated with computing the power spectrum of the space-dependent sample array, wherein the feature is one of or a function of one or more of the following:

1) the energy ratio between a group of low frequency components and a group of high frequency components within the power spectrum of the space-dependent sample array;

2) the energy ratio between a group of low frequency components and the total energy within the power spectrum of the space-dependent sample array;

3) the energy ratio between the spectrum element with the highest energy level and the total energy within the power spectrum of the space-dependent sample array;

4) the absolute frequency associated with the spectrum element with the highest energy level within the power spectrum of the space-dependent sample array; and 5) the lowest frequency associated with an element of the cumulative power spectrum of the space-dependent sample-array, whose energy is greater than (or equal to) a predefined constant times the total energy within the power spectrum of the space-dependent sample array.

The method may further comprise defining a stacked space-dependent sample array by stacking the space-dependent sample arrays for multiple volume-gates; wherein a space-dependent sample array is the result of arranging the space-dependent samples over the probe for a given volume-gate in an array, which may be one-dimensional, two-dimensional or multi-dimensional; and wherein at least one of the clutter suppression features is derived for each aligned volume-gate from the corresponding cells of the stacked space-dependent sample array.

A stacked space-dependent sample array may be the result of stacking the space-dependent sample arrays for multiple volume-gates, which is one or more of:

i) associated with different volume-gates in the same receive beam, arranged in an order corresponding to the distance of the corresponding volume-gates from the probe's surface, wherein the internal order of all space-dependent sample arrays is the same; and ii) associated with different receive beams, arranged in increasing or decreasing order of spatial angle (in one or more axes) and/or in increasing or decreasing order of cine-loop frame index;

wherein a stacked sample-array component is one or more of: (i) the magnitude, (ii) the phase, (iii) the real component, and (iv) the imaginary component, of the stacked space-dependent sample array.

The at least one of the clutter suppressions features may be computed from one or more of:

a certain statistic (e.g., mean, weighted mean, median, certain percentile) of the local stacked array spatial derivative within the stacked space-dependent sample array and/or the stacked sample-array component;

a certain statistic (e.g., mean, weighted mean, median, certain percentile) of a local blob slope within the stacked space-dependent sample array and/or the stacked sample-array component;

the number of diagonal zero-crossings;

the number of diagonal zero-crossings, divided by the number of the transducer elements (30) turned on.

When the at least one of the clutter suppression features is computed from a certain statistic of a local blob slope, the blob within a two-dimensional or multi-dimensional array may be a continuous spatial regions, including no zero-crossings within it but with zero-crossings and/or array boundaries at its boundaries.

The step of computing one or more clutter suppression features may further comprise applying a correction to the computed values of the clutter suppression features, wherein the correction for each aligned volume-gate depends on one or more of the following: the spatial angle between the boresight of the transmit beam and the boresight of the receive beam; the spatial angle between the receive beam's boresight and broadside; and the sample's distance from the probe's surface, measured along the path of the beam.

The metric value may either only depend on the values of clutter suppression features for the corresponding aligned volume-gate; or depend on the values of clutter suppression features for both the corresponding aligned volume-gate and additional aligned volume-gates, which may be at least one of spatially adjacent, on one or more axes or in any axis; and temporally adjacent.

The metric value may be a predefined function of the local values of one or more clutter suppression features.

The metric value may be an adaptively determined function of the local values of one or more clutter suppression features.

Computing the metric value may comprise computing one or more metric models, wherein each metric model is associated with a group of aligned volume-gates ("aligned volume-gate group") and one or more of the one or more clutter suppression features ("feature group"); and for each of the one or more aligned volume-gates, setting the local metric value in accordance with the value of one or more metric models, associated with the local value of the clutter suppression features.

The aligned volume-gate group may either includes all aligned volume gates in all frames, or may be a subset of the aligned volume-gates, associated with one or more of the following: a swath of range with respect to the probe's surface; a swath of beam phase centers over the probe's surface; a swath of spatial angles between the receive beam's boresight and broadside; a swath of spatial angles between the boresights of the transmit beam and the receive beam; and a time swath.

The local metric value may be based on one of the following: the metric models associated with the current aligned volume-gate group; or the metric models associated with the current aligned volume-gate group and one or more spatially and/or temporally adjacent aligned volume-gate groups.

Computing a metric model for an aligned volume-gate group may comprise computing the joint probability density function (joint-PDF) of the feature group associated with the metric model, taking into account only volume-gates associated with the volume-gate group associated with the metric model; and transforming the joint-PDF into a joint cumulative probability density function (joint-CDF).

The metric model may be described by the joint-CDF, and wherein determining the local metric value for an aligned volume-gate, based on the corresponding values for the feature group and a given metric model, comprises one of interpolation over the metric model, for coordinates matching the values for the feature group; and looking for the nearest neighbor within the metric model, for coordinates matching the values for the feature group.

Computing the metric model for an aligned volume-gate group may further comprise applying a transfer function to the joint-CDF, to obtain an adapted metric model, to be employed for metric value computation.

The transfer function may depend on one or more of the following parameters, derived from the joint-PDF and/or the joint-CDF:

the clutter suppression feature values associated with the joint-PDF peak, defined as one of the element within the joint-PDF whose value is highest, the center-of-mass of the joint-PDF; or the center-of-mass of the joint-PDF, after discarding all joint-PDF distribution modes other than the one with the highest peak and/or highest total probability; the clutter suppression feature values associated with the joint-PDF positive extended peak; and the clutter suppression feature values associated with the joint-PDF negative extended peak.

The beamforming summation step may be applied to the aligned volume-gates before, during or after applying matched filtering.

The beamforming summation step may depend on one of the metric value for the corresponding aligned volume-gate; and the metric value for both the corresponding aligned volume-gate and additional aligned volume-gates, which may be at least one of spatially adjacent, in one or more axes or in any axis; and temporally adjacent.

The beamforming summation step for each aligned volume-gate may depend on the result of applying a spatial low-pass filter to the metric values associated with the corresponding aligned volume-gate and spatially adjacent aligned volume-gates, associated with the same receive beam.

The beamforming summation step may comprise adaptively determining one or more of the following beamforming summation parameters depending on the metric value for the corresponding aligned volume-gate, and possibly also on the metric value for additional aligned volume-gates: the set of transducer elements (30) turned-on for the corresponding aligned volume-gate; the apodization pattern employed for the corresponding aligned volume-gate; a multiplier applied to all samples associated with the corresponding aligned volume-gate.

The clutter suppression function may be applied to the beamformed sample value before, during or after applying matched filtering.

The clutter suppression function may be one of depend on the metric value for the corresponding aligned volume-gate, and depend on the metric value for both the corresponding aligned volume-gate and additional aligned volume-gates, which may be at least one of: (i) spatially adjacent, either limiting the scope of the term "spatially adjacent" to one or more axes or in any axis; and (ii) temporally adjacent.

According to a second aspect of the invention there is provided a method of ultrasound imaging, said method comprising generating one or more transmit beams, wherein the boresight of each of the transmit beams points to a direction associated with a target region, for each transmit beam, generating one or more receive beams using a probe comprising a transducer array, for each receive beam or group of receive beams, sampling the received signal one or more times, wherein each sample is associated with a certain volume within the target region ("volume-gate"), and wherein multiple space-dependent samples are taken over the probe for each volume-gate; and processing the samples, said processing comprising, for one or more volume-gates, applying beamforming sample alignment and arranging the results in a stacked space-dependent sample array, detecting one or more blobs within the stacked space-dependent sample array, and for each such blob determining its boundaries, for at least one of the one or more blobs, computing one or more blob features, and for each blob for which blob features have been computed, applying a function to the values of the stacked space-dependent sample array elements associated with the blob ("blob function"), wherein the blob function depends on the values of the corresponding blob features.

Detecting one or more blobs and determining their boundaries may be performed using segmentation methods.

For each element of the stacked space-dependent sample array within the blob, the blob function output may be one of: dependent only on the value of said element and the values of the corresponding blob features; and. dependent on the values of the stacked space-dependent sample array for said element and elements in its spatial and/or temporal vicinity, as well as on the values of the corresponding blob features.

The beamforming sample alignment may comprise applying phase shifts and/or time-delays to the samples, associated with beamforming.

A stacked sample-array component may be one or more of: (i) the magnitude, (ii) the phase, (iii) the real component, and (iv) the imaginary component, of the stacked space-dependent sample array.

A space-dependent sample array may be the result of arranging the space-dependent samples over the probe for a given volume-gate in an array, which may be one-dimensional, two-dimensional or multi-dimensional.

The stacked space-dependent sample array may be the result of stacking the space-dependent sample arrays for multiple volume-gates.

The result of stacking the space-dependent sample arrays for multiple volume-gates may be one or more of associated with different volume-gates in the same receive beam, arranged in an order corresponding to the distance of the corresponding volume-gates from the probe's surface, wherein the internal order of all space-dependent sample arrays is the same; and associated with different receive beams, arranged in increasing or decreasing order of spatial angle (in one or more axes) and/or in increasing or decreasing order of cine-loop frame index.

Blobs within a two-dimensional or multi-dimensional array may be continuous spatial regions, each including no zero-crossings within it but with zero-crossings and/or array boundaries at its boundaries.

A blob feature may be indicative of at least one of the stacked array spatial derivative, defined as the spatial derivative of the stacked sample-array component along one or more axes other than the one corresponding to the distance from the probe's surface; and the blob slope in one or more axes, wherein the blob slope is defined as the difference between the orientation of the blobs within the stacked sample-array component and a plane perpendicular to the axis corresponding to the distance from the probe's surface.

The blob function may further depend on the local or regional signal-to-noise ratio (SNR).

Compounded transmission sequences may be employed, and the processing the samples may be performed in one of the following ways: separately for each transmitted pulse, wherein the resulting outputs are used as inputs for the compounding scheme associated with compounded transmission sequences; and following the application of the compounding scheme associated with compounded transmission sequences, wherein the compounding outputs are used as inputs for the processing the samples.

The processing the samples may further comprise adjusting the beamforming sample alignment in accordance with the local or regional values of the blob features.

The adjusting the beamforming sample alignment may effectively rotate slanted blobs so as to reduce the absolute value of their blob slope and enhance range resolution.

At least some of the values of the blob features may be recalculated in accordance with the adjusted beamforming sample alignment.

The adjusting the beamforming sample alignment may be applied either with respect to all blobs or with respect to only some of the blobs.

The adjusting the beamforming sample alignment may be applied only with respect to blobs where the absolute value of the slope is relatively small.

According to a third aspect of the invention there is provided a method of ultrasound imaging, said method comprising generating one or more transmit beams, wherein the boresight of each of the transmit beams points to a direction associated with a target region, for each transmit beam, generating one or more receive beams using a probe (26) comprising a transducer array (30), for each receive beam or group of receive beams, sampling the received signal one or more times, wherein each sample is associated with a certain volume within the target region ("volume-gate"), and wherein multiple space-dependent samples are taken over the probe for each volume-gate; and processing the samples, said processing comprising, for one or more volume-gates, applying beamforming sample alignment and arranging the results in a stacked space-dependent sample array, for one or more elements of the stacked space-dependent sample array, computing one or more local suppression features; and for the one or more elements of the stacked space-dependent sample array, applying a function to the values of the stacked space-dependent sample array ("local suppression function"), wherein the local suppression function depends on the values of the one or more local suppression features.

For each element of the stacked space-dependent sample array, the local suppression function output may be one of dependent only on the value of said element and the values of the corresponding local suppression features; and dependent on the values of the stacked space-dependent sample array for said element and elements in its spatial and/or temporal vicinity, as well as on the values of the corresponding local suppression features.

The beamforming sample alignment may comprise applying phase shifts and/or time-delays to the samples, associated with beamforming.

A stacked sample-array component may be one or more of: (i) the magnitude, (ii) the phase, (iii) the real component, and (iv) the imaginary component, of the stacked space-dependent sample array.

A space-dependent sample array may be the result of arranging the space-dependent samples over the probe for a given volume-gate in an array, which may be one-dimensional, two-dimensional or multi-dimensional.

The stacked space-dependent sample array may be the result of stacking the space-dependent sample arrays for multiple volume-gates.

The result of stacking the space-dependent sample arrays for multiple volume-gates may be one or more of associated with different volume-gates in the same receive beam, arranged in an order corresponding to the distance of the corresponding volume-gates from the probe's surface, wherein the internal order of all space-dependent sample arrays is the same; and associated with different receive beams, arranged in increasing or decreasing order of spatial angle (in one or more axes) and/or in increasing or decreasing order of cine-loop frame index.

Each local suppression feature may be indicative of at least one of the local stacked array spatial derivative, defined as the spatial derivative of the stacked sample-array component along one or more axes other than the one corresponding to the distance from the probe's surface; and the local estimation of a blob slope in one or more axes, wherein the blob slope is defined as the difference between the orientation of the blobs within the stacked sample-array component and a plane perpendicular to the axis corresponding to the distance from the probe's surface.

Blobs within a two-dimensional or multi-dimensional array may be continuous spatial regions, each including no zero-crossings within it but with zero-crossings and/or array boundaries at its boundaries.

The local suppression function may be either predefined or adaptively determined according to the local or regional values of the local suppression features.

The local suppression function may further depend on the local or regional signal-to-noise ratio (SNR).

Compounded transmission sequences may be employed, and the processing of the samples may be performed in one of the following ways: separately for each transmitted pulse, wherein the resulting outputs are used as inputs for the compounding scheme associated with compounded transmission sequences; and following the application of the compounding scheme associated with compounded transmission sequences, wherein the compounding outputs are used as inputs for the processing the samples.

The processing the samples may further comprise adjusting the beamforming sample alignment in accordance with the local or regional values of the local suppression features.

The adjusting the beamforming sample alignment may effectively rotate slanted blobs so as to reduce the absolute value of their blob slope and enhance range resolution.

At least some of the values of the local suppression features may be recalculated in accordance with the adjusted beamforming sample alignment.

The adjusting the beamforming sample alignment may be applied either with respect to all elements of the stacked space-dependent sample array, or with respect to only some of the elements of the stacked space-dependent sample array.

The adjusting the beamforming sample alignment may be applied only to elements of the stacked space-dependent sample array whose local suppression features are indicative of relatively low absolute values of the blob slope.

According to a fourth aspect of the invention there is provided an apparatus for ultrasound imaging, comprising a probe, which is adapted to transmit ultrasonic radiation and to receive the reflected ultrasonic radiation, and a scanner, wherein the apparatus is operable to perform a method according to any of the preceding aspects of the invention.

BRIEF DESCRIPTION OF THE DRAWINGS

The invention for clutter suppression in ultrasonic imaging systems is herein described, by way of example only, with reference to the accompanying drawings.

With specific reference now to the drawings in detail, it is emphasized that the particulars shown are by way of example and for purposes of illustrative discussion of the embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF EMBODIMENTS

Figure 1A:
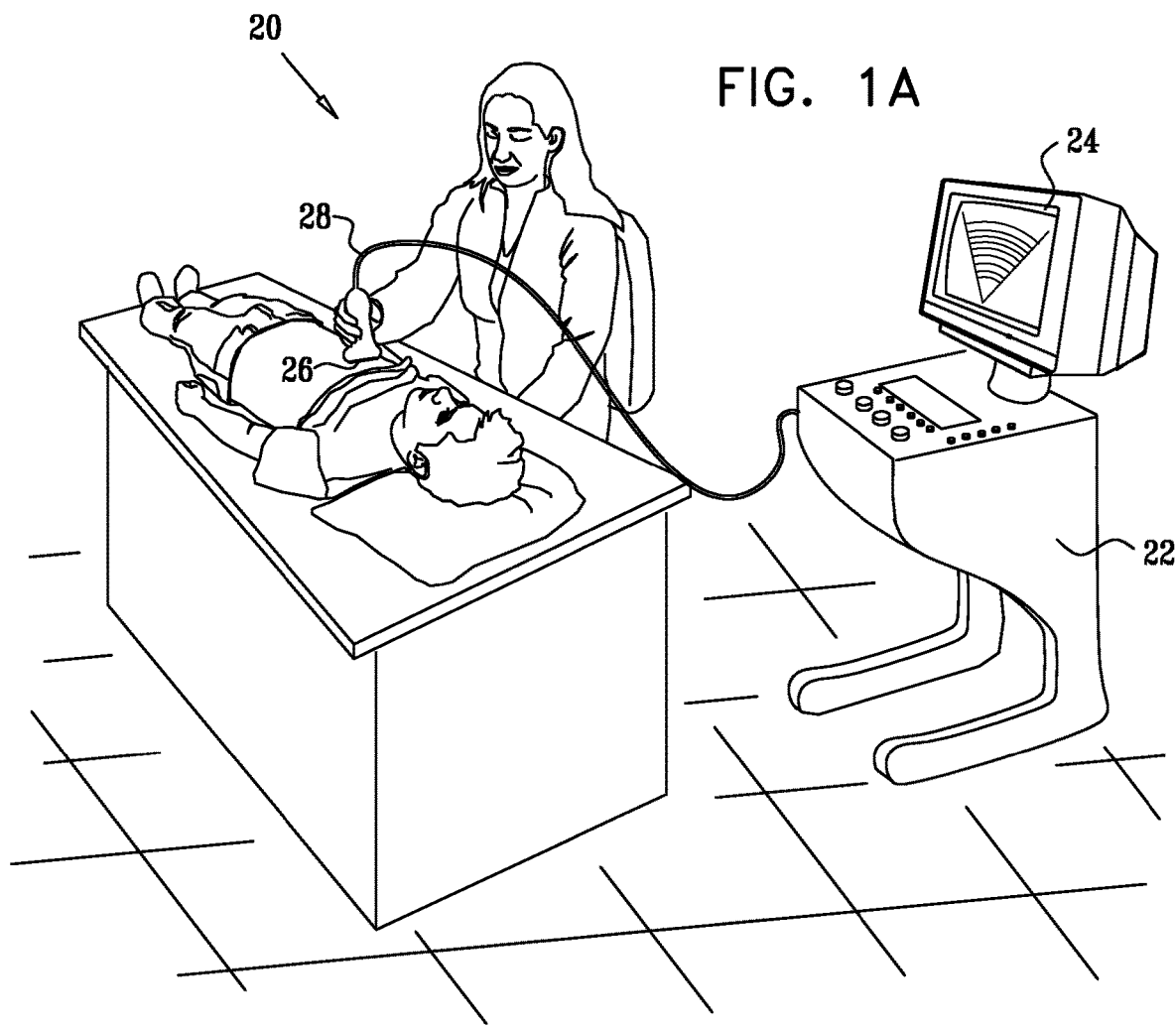
FIG. 1A is a schematic, pictorial illustration of an ultrasonic imaging system, in accordance with an embodiment of the present invention.

In broad terms, the present invention relates to methods and systems for suppressing clutter effects in ultrasonic imaging systems.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

System Description

FIG. 1A is a schematic, pictorial illustration of an ultrasonic imaging system 20, in accordance with an embodiment of the present invention.

System 20 comprises an ultrasound scanner 22 that scans target regions, e.g., organs of a patient, using ultrasound radiation. A display unit 24 displays the scanned images. A probe 26, connected to scanner 22 by a cable 28, is typically held against the imaged object, e.g., the patient body, in order to image a particular target region. Alternatively, the probe may be adapted for insertion into the imaged object, e.g., transesophageal or transvaginal imaging in medical applications. The probe transmits and receives ultrasound beams required for imaging. Probe 26 and/or scanner 22 comprise control and processing circuits for controlling probe 26 and processing the signals received by the probe.

Figure 1B:
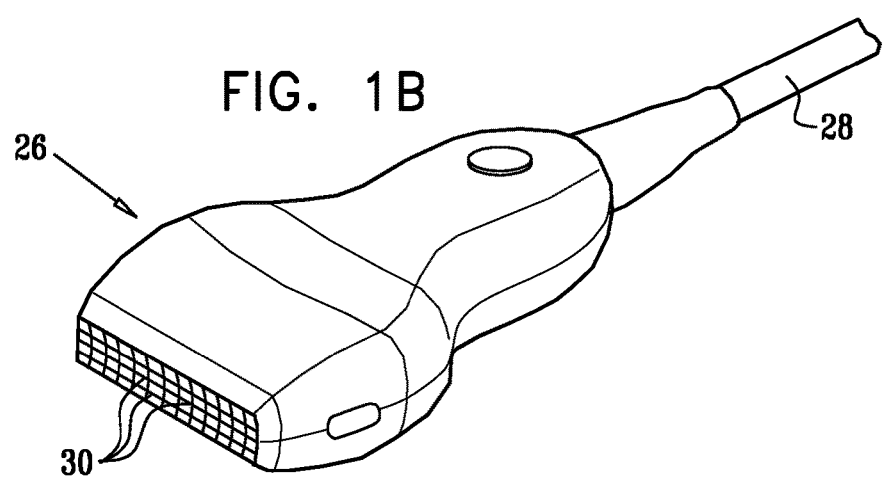
FIG. 1B is a schematic, pictorial illustration of a probe used in an ultrasonic imaging system, in accordance with an embodiment of the present invention.

FIG. 1B is a schematic, pictorial illustration of probe 26 used in imaging system 20, in accordance with an embodiment of the present invention. The probe includes an array of transducers 30, e.g., piezoelectric transducers, which may be configured to operate as a phased array. On transmission, the transducers convert electrical signals produced by scanner 22 into a beam of ultrasound radiation, transmitted into the target region. On reception, the transducers receive the ultrasound radiation reflected from the target region, and convert it into electrical signals, which are further processed by probe 26 and/or scanner 22.

The processing applied on reception typically comprises:
i) Beamforming, that is, compounding the reflected signals reaching each of the transducers in transducer array 30 and converted into electrical signals, to obtain a signal associated with an acoustic beam resulting from said reflected signals. The beam may be focused or unfocused.

When using pulsed-wave (PW) transmissions, the time delay between pulse transmission and signal reception is indicative of the distance R between the probe's surface and the spatial location within the imaged object from which the signal has been reflected (the description is accurate assuming a single reflection, without scattering or multi-path). Using the simplistic assumption of a constant speed of sound c within the medium, the time delay between pulse transmission and signal reception simply equals 2R/c. In some systems 20, the reception focus may be set to vary as a function of time since pulse transmission, so as to optimize the reception beam width along the beam path ("adaptive focusing"); and ii) Matched filtering. For example, when transmitting a pulse with a constant carrier frequency $f_c$, the matched filtering may comprise mixing the received signal with a reference signal, being a cosine signal coherently matching the frequency and phase of the transmitted signal, and applying a temporal low-pass filter to the output (mixing two pure cosine signals results in the sum of two cosine signals, one whose frequency matches the difference between the mixed signals' frequencies, and another whose frequency matches the sum of the mixed signals' frequencies; the low-pass filter discards the latter component), to obtain a matched filter output signal, referred to herein as the "real matched-filtered signal". Similarly, when transmitting a coded pulse, the complex conjugate of the transmitted signal is used as the reference signal.

Some systems also mix the received signal with a second reference signal, having the same frequency (as a function of time) as the first reference signal but shifted in phase by 90°, and apply a temporal low-pass filter to the output, to obtain a second matched filter output signal. The result of summing, for each time index, the first matched filter output signal with the second matched filter output signal multiplied by j (the square root of minus one), is referred to as the "complex I/Q signal" (the I stands for "in-phase", and the Q stands for "quadrature").

Both the real matched-filtered signal and the complex I/Q signal may be employed in a wide variety of applications. If necessary, simple transformations between the real matched-filtered signal and the complex I/Q signal are known in the art. For example, one may apply the Hilbert transform to the real matched-filtered signal, to obtain the complex I/Q signal.

Similarly, the real component of the complex I/Q signal can be used as the real matched-filtered signal. Note that the number of samples associated with the complex I/Q signal is twice as high as the number of samples associated with the real matched-filtered signal, so interpolation along the range axis may be required prior to discarding the imaginary component of the complex I/Q signal, in order to retain the information within the complex I/Q signal.

Also note that certain systems employ complex signals even before applying matched filtering ("complex pre-matched-filtering signals"). Such complex pre-matched-filtering signals may be produced by concurrently sampling each signal with two analog-to-digital converters, with a 90° phase difference between them (with respect to the reference signal); alternatively, the Hilbert transform may be applied to the real samples.

Both the beamforming and the matched filtering may be applied analogically, digitally or in a combined fashion (digital processing is applied to the signal after analog-to-digital conversion). Furthermore, both beamforming and matched filtering may be performed in one or more steps, and the order between the different steps of beamforming and matched filtering may vary between different systems. For instance, matched filtering may be applied before beamforming, e.g., to the signal associated with each transducer in transducer array 30, or to the beamformed signal.

Additional processing applied on reception is often specific to the mode of operation of system 20. For example, when generating gray-scale images of the target region morphology as a function of time, in A-mode, B-mode or M-mode, transforming each signal sample after beamforming into a displayed videointensity may include at least one of the following steps, in any order:
i) Determining the magnitude of the signal's envelope. For complex I/Q samples, this can be performed by applying an absolute operator;
ii) Converting the signal to logarithmic units (a process referred to as "log-compression");
iii) Applying a transfer function to the signal;
iv) Replacing all values lower than a minimal value by the minimal value, and/or all values higher than a maximal value by the maximal value; and
v) Scaling the signal in accordance with the displayed dynamic range.

Displaying the information may further include "scan conversion", that is, converting the data from the data acquisition coordinates to the coordinates of the display unit 24. In echocardiography, for instance, data acquisition typically employs polar coordinates, wherein a plurality of beams are transmitted at different spatial angles, all having the same phase center (the term is defined herein below), and for each such beam one or more receive beams are generated, and for each receive beam multiple samples are made, each matching a different distance from the probe's surface; conversely, the display coordinates are typically Cartesian.

Additional or different processing may be applied for Doppler-based modes of operation.

Probe Designs

Probe 26 typically comprises several dozens and up to several thousands of transducers 30. As a rule of thumb, the probe's beam width along a given axis is proportional to the ratio between the transmitted wavelength and the probe's effective size along that axis. For wideband signals, the beam width varies from one wavelength to the next, and is often estimated using a typical transmitted wavelength, e.g., the mean wavelength. The "effective size" of the probe is affected by the probe's physical dimensions, but also by the amplitudes of the weights assigned to the different transducers during beamforming (as described herein below).

The long-axis of the transducer array will be referred to as the "horizontal axis" or the "azimuth axis", whereas the short-axis of the transducer array will be referred to as the "vertical axis" or the "elevation axis". In cases where the probe is symmetrical to 90 degree rotation, one of the probe's primary axes will arbitrarily be selected as the "horizontal axis" or "azimuth axis".

In "one-dimensional probes," the transducers are arranged in a one-dimensional array, where the transducer centers are placed along a straight line or a curved line, e.g., a convex curve. "1½ dimensional probes" comprise several rows of transducers in the vertical dimension, providing a vertical sector-like beam pattern. "Two-dimensional probes" comprise a complete two-dimensional (or multi-dimensional) array of transducers, enabling control over both horizontal and vertical directional beam patterns.

Probe 26 may further comprise an acoustic lens, typically situated between the transducers and the target region. For example, in one-dimensional probes, the vertical beamwidth is often adjusted by an acoustic lens.

The transducer array 30 may be stationary, or may be mechanically scanned. For example, in one-dimensional and 1½ dimensional probes, the transducer array 30 may be mechanically scanned along the vertical axis, to complement the electronic scanning made along the horizontal axis.

Beamforming

Each transmit or receive beam may be characterized by a phase center, a beam pattern, and a boresight.

The "phase center" is defined as the point along the surface of transducer array 30 from which the beam emanates. When using unfocused beams, the phase center may be ill-defined, in which case it can be defined arbitrarily, e.g., at the center of the probe.

The "beam pattern" is defined as the probe's gain as a function of spatial location. In many cases, the medium is not known a-priori, and the beam pattern is computed assuming that the propagation is within a homogeneous medium, without taking into account physical effects such as reflection, refraction, attenuation, scattering, diffraction, and the like. Note that, is certain cases, the beam pattern computed for a homogeneous medium is assumed to change only with the spatial angle (e.g., in the far-field of the receive beam, when the receive focus is constant, i.e., not adaptive), whereas in other cases the beam pattern changes as a function of time since pulse transmission as well, that is, with the distance from the probe's surface (e.g., in the near-field of the receive beam, and/or when using adaptive focusing on reception). In other cases, the beam pattern is computed for a given medium. The term "mainlobe" refers to the swath of spatial angles including the highest peak of the beam pattern, wherein if we start at the spatial angle associated with the highest probe gain and continuously scan in any direction, we remain within the mainlobe as long as we have not yet reached a null or a dip. Other gain peaks within the beam pattern are referred to as "sidelobes".

The "boresight" is the unit-vector pointing from the beam's phase center to the center of the beam's mainlobe. The "broadside" is often used as reference for the boresight, wherein the broadside is a unit-vector perpendicular to the surface of the transducer array, emanating from the beam's phase center.

The process of beamforming is based on applying phase shifts and/or time delays to the signals associated with each transducer 30. Phase-shift based beamforming is typically employed when the bandwidth of the transmitted signal is much lower than the carrier frequency, so that phase shifts are well defined.

To describe one common form of phase-shift based beamforming on reception, let k be the transducer index (k should go over all transducers even if the transducer array comprises more than one dimension), $s_k$ be the signal measured by transducer k (which may be analog or digital, before or after matched filtering, real or complex), $a_k$ be an apodization coefficient of transducer k on reception, $\varphi_k$ be the phase shift for transducer k on reception, and j be the square root of minus one. The beamformed signal S at time t may be computed using eq. (1):

$$S(t)=\Sigma_k a_k(t) e^{j\varphi_k(t)} s_k(t) \qquad (1)$$

Alternatively, when using time-delays instead of phase shifts, where $\tau_k$ is the time-delay for transducer k, one may use eq. (2) for beamforming on reception:

$$S(t)=\Sigma_k a_k(t) s_k(t-\tau_k) \qquad (2)$$

Similar equations may be used for combined time-delay and phase-shift design. Comparable equations may also be utilized on transmission.

The phase shifts $\varphi_k$ and/or the time-delays $\tau_k$ determine the beam's boresight, and also affect the beam pattern. The apodization coefficients $a_k$ are usually real, and are typically used for adjusting the beam pattern.

The apodization coefficients $a_k$ have a very similar effect to windows employed in spectral analysis, e.g., when applying discrete Fourier transform (DFT) to digital signals. Various windows known in spectral analysis, e.g., Hamming, Blackman, or Taylor windows can be employed as the apodization pattern. Based on Fourier optics principles, the far-field beam pattern as a function of spatial angle can be estimated based on applying a Fourier transform to the probe's aperture, taking into account the power distribution over the aperture on transmission, or the relative sensitivity distribution over the aperture on reception. The power distribution or sensitivity distribution are determined by the apodization coefficients.

Generally speaking, not all transducers are necessarily employed all the time. Currently used transducers are referred to as "turned-on", whereas unused transducers are "turned-off". Turned-off transducers are assigned an apodization coefficient 0, whereas turned-on transducers are typically assigned apodization coefficients ranging from 0 to 1. The values of the apodization coefficients over all transducers 30 ("apodization pattern") may affect the width of the beam's mainlobe as well as attributes of the beam's sidelobes (e.g., the gain ratio between the peak of the highest sidelobe and the peak of the mainlobe is referred to as the "peak-sidelobe ratio").

For unfocused beams, the receive phase shifts and/or time delays are typically set so as to make sure that the phase corrected and/or time shifted signals originating from points on a plane perpendicular to the boresight would reach all transducer elements 30 at the same time and/or phase. For focused beams, the receive phase shifts and/or time delays are typically set so as to make sure that the phase corrected and/or time shifted signals originating from the focal point would reach all transducer elements 30 at the same time and/or phase. Similar methodology is applied on transmission.

Figure 2A:
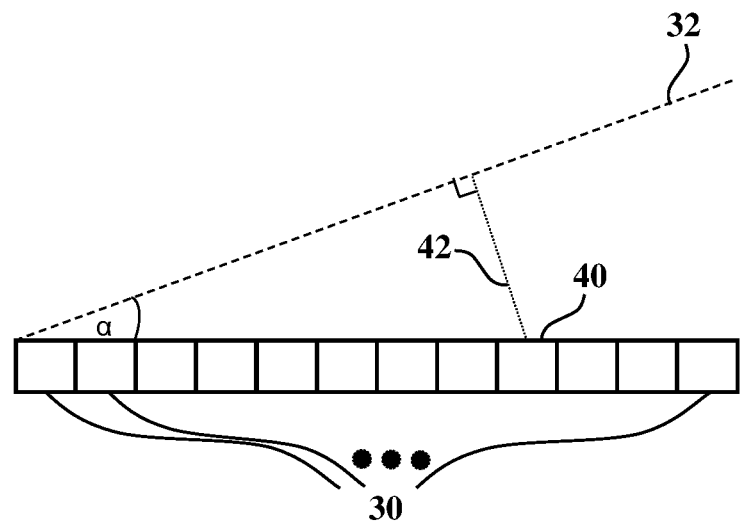
FIG. 2A is a schematic, pictorial illustration of the method for setting the phase shifts and/or time delays when generating unfocused beams using one-dimensional linear probes, in accordance with an embodiment of the present invention.

For example, for a one-dimensional linear probe, a possible scheme for setting the phase shifts and/or time delays to form unfocused receive beams is demonstrated in FIG. 2A. Let $\alpha$ be the angle between the surface of transducer array 30 and the required wave-front plane 32, which also equals the angle between the beam's boresight and its broadside. With phase-shift based beamforming, for a given element 40 of transducer array 30, denoted as element k, the one-way phase shift $\varphi_k$ is set to match the distance 42 from the center of element 40 to the required wave-front plane 32:

$$\varphi_k = \mathrm{mod}\left(\frac{2\pi}{\lambda}kD\sin(\alpha), 2\pi\right) \quad (3)$$

wherein $\lambda$ is the transmitted wavelength, D is the distance between the centers of adjacent transducer elements, and mod is the modulus operator.

With time-delay based beamforming, for a given element 40 of transducer array 30, denoted as element k, the one-way time-delay $\tau_k$ is likewise set to match distance 42 from the center of element 40 to the required wave-front plane 32:

$$\tau_k = \frac{kD\sin(\alpha)}{c} \quad (4)$$

wherein c is the estimated speed of sound within the medium.

Figure 2B:
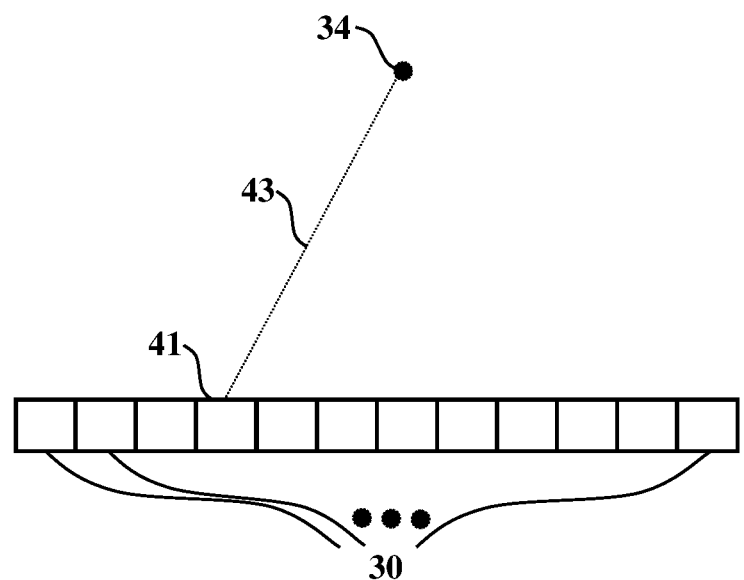
FIG. 2B is a schematic, pictorial illustration of the method for setting the phase shifts and/or time delays when generating focused beams using one-dimensional linear probes, in accordance with an embodiment of the present invention.

Similarly, for a one-dimensional linear probe, a possible scheme for setting the phase shifts and/or time delays to form focused receive beams is demonstrated in FIG. 2B. With phase-shift based beamforming, for a given element 41 of transducer array 30, denoted as element k, the one-way phase shift $\varphi_k$ follows eq. (5):

$$\varphi_k = \mathrm{mod}\left(\frac{2\pi}{\lambda}R_k, 2\pi\right) \quad (5)$$

wherein $\lambda$ is the transmitted wavelength, $R_k$ is the distance 43 from the focal point 34 to the center of element k.

With time-delay based beamforming, for a given element 41 of transducer array 30, denoted as element k, the one-way time-delay $\tau_k$ follows eq. (6):

$$\tau_k = \frac{R_k}{c} \quad (6)$$

A single array of transducers may generate beams with different phase centers, boresights and beam patterns. Furthermore, some systems 20 concurrently use on reception, for a single transmitted pulse, more than one set of apodization coefficients $a_k$ and/or more than one set of phase shifts $\varphi_k$ and/or more than one set of time-delays $\tau_k$. This setting is commonly referred to as multi-line acquisition, or MLA. In MLA configurations, the beam pattern used on transmission is sometimes wider than those used on reception, so as to provide sufficient ultrasound energy to most or all of the volume covered by the different concurrent receive beams.

Further types of systems 20 use multiple concurrent beams on transmission. Examples for relevant architectures of system 20 are described herein below.

Beamforming Architectures

Beamforming may be achieved using different system architectures. Two common architectures are "analog beamforming" (ABF) and "digital beamforming" (DBF). Note that some systems 20 employ ABF in one probe axis and DBF in the other.

In ABF, beamforming is applied analogically, e.g., using eq. (1) and/or eq. (2), and sampling is applied after beamforming; however, matched filtering may be applied analogically, digitally or in a combined fashion. The number of concurrent receive beams per transmitted beam is typically determined prior to pulse transmission, and is usually equal to or lower than the number of analog-to-digital converters (ADCs) available. The parameters of each such receive beam are also determined prior to sampling.

In DBF, at least some beamforming steps are performed digitally. Sampling is applied either before beamforming or after some but not all beamforming steps; matched filtering may still be applied analogically, digitally or in a combined fashion. In some configurations, an ADC is assigned to each element of transducer array 30; this configuration is commonly referred to as "per-channel sampling". In other configurations, an ADC is assigned to groups of adjacent elements of transducer array 30, wherein each such group is referred to as a "sub-array". The term "sub-array" may also refer to a group of elements of transducer array 30 including a single element or the entire transducer array. When using per-channel sampling, all beamforming steps are typically digital, whereas with sub-arrays, the beamforming may be partly digital and partly analog. DBF allows great beamforming flexibility, for instance, selecting the number of receive beams and their parameters after sampling. DBF typically involves very high data rates, necessitating relatively advanced hardware.

In both ABF and DBF, the beamforming may be performed by probe 26, scanner 22, or a combination thereof. Furthermore, beamforming parameters may change over time. For example, during scanning, the beams used on transmission and/or reception may employ varying phase centers, boresight directions or beam patterns. In addition, with adaptive focusing, the phase-shifts and/or time-delays vary during the reception of signals for a given transmitted pulse, changing in accordance to the reception focus. Some systems 20 also synchronously change the apodization pattern with the reception focus.

In DBF, one may divide the beamforming processing into two groups of steps:
i) "Beamforming sample alignment"—includes applying the phase-shifts and/or time delays to the samples, and possibly applying the apodization coefficients;
ii) "Beamforming summation"—comprises summing over the samples associated with the different elements or sub-arrays of transducer array 30, and possibly applying the apodization coefficients beforehand.

Another well-known system configuration employs a synthetic aperture, that is, the full probe aperture on transmission and/or reception is generated using multiple transmitted pulses. In some synthetic aperture systems 20, each transmit pulse employs a single element or a certain sub-array of transducer array 30, and the same element or sub-array is used on reception for that pulse. In other synthetic aperture systems 20, each transmit pulse employs a single element or a certain sub-array of transducer array 30, wherein on reception a certain element or sub-array is employed, which may not match the transmit sub-array; alternatively, the entire transducer array 30 may be used on reception. In further synthetic aperture systems 20, each transmit pulse employs the entire transducer array 30, but subsets of transducer array 30 are used on reception.

An additional system design known in the art employs multiple concurrent transmitted beams ("multiple orthogonal excitations"). On transmission, some or all elements of transducer array 30 are fed the sum of two or more signals, each associated with a different transmit beam, and each having a different waveform, e.g., different central transmission frequency and/or different pulse encoding configuration. In these cases, each receive beam is typically generated using a specific matched filter, corresponding to one of the transmission waveforms.

A further system design known in the art is based on assigning orthogonal waveforms to different elements or sub-arrays of transducer array 30 during transmission ("orthogonal sub-array coded excitation"). Typically, at least two of the orthogonal waveforms employ the same frequency band. On reception, each element or sub-array of transducer array 30 may apply matched-filtering to more than one waveform, yielding signals associated with pairs of transmit elements/sub-arrays and receive elements/sub-arrays. As a result, the beamforming equations for both transmission and reception may be applied during processing ("two-way beamforming by processing"). This allows the flexibility of adaptively determining the transmit beam pattern, for example for adaptive focusing on transmission, in addition to reception. This configuration is described, for example, by Zheng et al., in a paper entitled "Novel Transmit Aperture for Very Large Depth of Focus in Medical Ultrasound B-Scan," IEEE Transactions on Ultrasonics, Ferroelectrics, and Frequency Control, vol. 53, 2006, pages 1079-1087.

Even further system designs perform adaptive focusing on transmission without using multiple orthogonal waveforms. An example for such a system design, which combines data associated with multiple transmit beams, is described in U.S. patent application 2015/0049578, by Hoctor et al., published on Feb. 19, 2015, titled "Systems and Methods for Ultrasound Retrospective Transmit Focus Beamforming."

Certain system configurations employ transmission sequences wherein multiple pulses are transmitted using the same phase center, beam pattern, and boresight, but the transmission waveform is not the same in all pulses. For each range-gate, the samples associated with the different transmitted pulses (either after beamforming sample alignment or after beamforming) are then compounded to obtain a certain goal. Such sequences shall be referred to herein as "compounded transmission sequences".

One such sequence is called "pulse inversion". It employs pairs of transmission pulses, wherein the transmitted waveform of the second pulse is the complex conjugate of the transmitted waveform of the first pulse. For each range-gate, the samples for the two pulses are then coherently summed. This results in significant attenuation of linear components of the received signal, whereas non-linear components are less affected. For example, in contrast imaging, pulse inversion enhances the distinction between contrast agents and surrounding tissues, since contrast agents are characterized by significant non-linear response.

Target Region Scanning

In some modes of operation of system 20, all data acquired is associated with the same volume within the target region. This applies, for example, to many continuous wave (CW) Doppler studies in medical imaging.

In other modes of operation, different measurements made are associated with different volumes within the target region.

As mentioned herein above, with PW transmission, the time delay between pulse transmission and signal reception is indicative of the distance R between the probe's surface and the spatial location within the imaged object from which the signal has been reflected. As a result, for each receive beam, the data may be arranged in "range-gates", each associated with a different distance R. After beamforming, there is a single sample for each range-gate, which may be real (e.g., real sample before matched-filtering, or real matched-filtered signal) or complex (e.g., complex pre-matched-filtering signal, or complex I/Q signal). Before or during beamforming, when using per-channel sampling or sampling per sub-array, the number of samples for each range-gate is typically higher; for example, when the receive beam does not employ orthogonal sub-array coded excitation or synthetic aperture, the number of samples for each range-gate equals the number of elements of transducer array 30 used (for per-channel sampling) or the number of sub-arrays used (for sampling per sub-array). As a further example, when using orthogonal sub-array coded excitation with M orthogonal codes (which are applicable to the receive beam), after matched filtering, the number of samples per range-gate equals M times the number of elements of transducer array 30 used (for per-channel sampling) or the number of sub-arrays used (for sampling per sub-array).

When multiple samples are associated with each range-gate, one can define two types of range-gates: (i) "pre-aligned range-gates", including for each range-gate the samples before beamforming sample alignment; and (ii) "aligned range-gates", including for each range-gate the samples after beamforming sample alignment but before beamforming summation.

With CW transmission, the time delay between pulse transmission and signal reception may be undefined, so one cannot differentiate reflections from different range-gates. However, using coded CW transmission, e.g., frequency modulation CW (FMCW), yields range-dependent information when applying appropriate matched filtering.

Moreover, data acquisition may comprise scanning transmit and/or receive beams over time. The scanning classically involves changing one of more of: (i) the beam's phase-center; and (ii) the beam's boresight. When using PW signals or coded CW signals on transmission, for each receive beam, one or more samples are taken for each range-gate. The data acquisition coordinates, and the arrangement of the samples, are defined accordingly. For example, in echocardiography, B-scan usually involves the phase center being kept constant, whereas the receive beam boresight is scanned to cover a two-dimensional (2D) or three-dimensional (3D) sector. The samples are thus arranged using polar coordinates (for 2D sectors) or spherical coordinates (for 3D sectors). In another example, with linear probes employed in general imaging, the typical B-scan configuration involves the phase center being scanned from side to side over time, and all receive beams are approximately perpendicular to the probe's surface. The samples are thus arranged using 2D or 3D Cartesian coordinates.

Furthermore, data acquisition may involve repeated scanning of the same target region, so as to provide time-dependent information regarding said target region. The information associated with each single scan of the target region is referred to as a "frame".

The information displayed on display unit 24 is transformed to match the display's coordinate system. In 2D imaging, the term "pixel" refers to a picture element associated with a certain volume within the imaging plane at a certain time. In 3D imaging, the term "voxel" refers to a picture element associated with a certain volume within the imaging volume at a certain time. In the context of this disclosure document, the term "pixel" will be extended to refer both to a pixel and to a voxel. For example, in M-mode scanning, used in medical imaging, the receive beam phase center and boresight are typically kept constant, and the signal is displayed as a function of distance from the probe's surface and of time. Conversely, in B-scan, different frames are usually displayed one after the other, in the order of data acquisition.

Data Acquisition Configurations for Clutter Suppression

In embodiments of the present invention, data acquisition involves:
 i) Generating one or more transmit beams, wherein each such transmit beam is associated with transmitting a PW or a CW signal;
 ii) For each transmit beam, generating one or more receive beams; and
 iii) For each receive beam, sampling the received signal one or more times, wherein each sample is associated with a certain volume within the target region ("volume-gate"). For PW or coded CW transmitted signals, each volume-gate is a range-gate; whereas for un-coded CW transmitted signals, each volume-gate corresponds to the volume covered by the entire two-way beam-pattern of the applicable transmit beam and receive beam.

Note that the use of the term "volume-gate" should not be construed as limiting the scope of the description to three-dimensional data acquisition. In fact, the different volume-gates may span a spatial point, a line, a plane, or a volume.

In some embodiments, the sampling is performed prior to applying matched filtering, whereas in other embodiments, the sampling is performed after applying matched filtering. In certain embodiments, the sampling is real, and in others the sampling is complex.

In some embodiments, the sampling is performed prior to beamforming, and in other embodiments the sampling is performed after beamforming.

The processing associated with the present invention requires that, for each volume-gate, "multiple space-dependent samples over the probe" would be taken. That is, for each volume-gate, multiple samples would be taken, wherein each sample or group of samples is associated with at least one of: (i) a different receiving element of transducer array 30; (ii) a different receiving sub-array of transducer array 30; and (iii) a different phase center. This can be achieved in various ways, for instance:
 i) Using per-channel sampling, in which case each of the multiple space-dependent samples over the probe is associated with a different receiving element of transducer array 30 (samples may be stored for all elements or only for elements turned-on);
 ii) Sampling per sub-array, in which case each of the multiple space-dependent samples over the probe is associated with a different receiving sub-array of transducer array 30 (samples may be stored for all sub-arrays or only for sub-arrays which are turned-on);
 iii) Generating two or more receive beams, each having a different phase center, applying beamforming for each such receive beam, and collecting the data associated with each volume-gate together to obtain the multiple space-dependent samples over the probe. Note that the two or more receive beams may be associated with one or more transmit beams;
 iv) Using synthetic aperture data acquisition, wherein each transmit pulse uses a single element or a certain sub-array of transducer array 30, and the same element or sub-array is used on reception for that pulse ("basic synthetic aperture data acquisition"). After transmitting a series of pulses covering the relevant section of transducer array 30, the data associated with each volume-gate should be collected together to obtain the multiple space-dependent samples over the probe;
 v) Using synthetic aperture data acquisition, wherein each transmit pulse employs a single element or a certain sub-array of transducer array 30, and on reception, for each transmit pulse, a certain element or sub-array or the entire transducer array 30 is employed, wherein the set of elements used on transmission and the set of elements used on reception do not always match ("extended synthetic aperture data acquisition"). After transmitting a series of pulses covering the relevant section of transducer array 30, the data associated with each volume-gate should be collected together to obtain the multiple space-dependent samples over the probe; and
 vi) Using orthogonal sub-array coded excitation, with per-channel sampling or sampling per sub-array. After applying all applicable matched filters, the data associated with each volume-gate should be collected together to obtain the multiple space-dependent samples over the probe.

Note that, when using options (i)-(v), multiple orthogonal excitations may also be employed.

Also note that, when using option (iii), the multiple space-dependent samples over the probe for each volume-gate result from beamformed data associated with multiple receive beams. When using the other options, the multiple space-dependent samples over the probe for each volume-gate correspond to data before beamforming. When using data before beamforming, the acquired data for each volume-gate may be used in one or more concurrent receive beams.

Fundamental Clutter Suppression Concepts

When the multiple space-dependent samples over the probe for each volume-gate correspond to data before beamforming, let us define "aligned volume-gates" as volume-gate data after beamforming sample alignment but before beamforming summation. For PW or coded CW transmitted signals, aligned volume-gates correspond to the previously defined aligned range-gates.

When the multiple space-dependent samples over the probe for each volume-gate correspond to data after beamforming (see option (iii) above), let us define "aligned volume-gates" as the output of collecting the data associated with each volume-gate together to obtain the multiple space-dependent samples over the probe.

The inventor has discovered that, when acquiring multiple space-dependent samples over the probe for each volume-gate, aligned volume-gates including mostly desired information (and therefore little or no clutter contribution) demonstrate one or more of the following characteristics ("desired information characteristics"):

i) When beamforming sample alignment involves perfect focusing, a single reflector located at the center of the current volume-gate (completely clutter-free case) should result in approximately constant space-dependent samples over the probe; some variability may be introduced by differences in gain for the current volume-gate (e.g., in per-channel sampling, the element pattern of different elements may result in slightly different gains for each transducer element 30).

In practical cases, physical effects such as scattering along the path of the beam further increase the signal variability of the space-dependent samples over the probe ("probe spatial variability"), wherein the variability can be seen in one or more of: (a) the signal magnitude; (b) the signal phase; (c) the signal's real component; and/or (d) the signal's imaginary component. However, the probe spatial variability is typically lower for aligned volume-gates including mostly desired information than for aligned volume-gates with significant clutter contribution. This stems from the fact that signals originating from spatial angles and/or ranges far from the center of the current volume-gate are not focused correctly in the process of beamforming sample alignment, so their beamforming phase shifts and/or time-delays are imprecise, thus increasing the probe spatial variability.

When arranging the space-dependent samples over the probe for a given volume-gate in an array ("space-dependent sample array"), wherein the space-dependent sample array may be:

a. One-dimensional. For example, in per-channel sampling or in basic synthetic aperture data acquisition, the array element index may correspond to the index of the corresponding element of transducer array 30;

b. Two-dimensional. For example, when using two-dimensional probes with per-channel sampling, the row and column index can match the row and column index of the corresponding element of transducer array 30; or c. Multi-dimensional. This configuration is useful, for instance, with orthogonal sub-array coded excitation;

the probe spatial variability can be evaluated using various attributes (features), which may belong to one or more of the following attribute groups:

a. The standard deviation or variance of the space-dependent sample array, taking into account one or more of the following components of the array's signal: magnitude, phase, real component, and/or imaginary component. Low values are associated with low probe spatial variability, and therefore low local clutter level and/or low local probability for the aligned volume-gate to be significantly affected by clutter;

b. A certain statistic (e.g., mean, median, predefined percentile) of the spatial derivatives within the space-dependent sample array, taking into account one or more of the following components of the array's signal: magnitude, phase, real component, and/or imaginary component. The term "spatial derivative" here may refer to any derivative, e.g., first or second derivative. When the space-dependent sample array is two-dimensional or multi-dimensional, said spatial derivatives may be in one or more axes of the space-dependent sample array, wherein each axis may be, but does not have to be, aligned with one of the probe's primary axes. Low values are associated with low probe spatial variability;

c. A feature associated with counting zero-crossings within the space-dependent sample array. When the space-dependent sample array is real, a zero-crossing is defined as a sign change between adjacent array elements and/or the occurrence of a value being very close to 0. When the space-dependent sample array is complex, a zero-crossing is defined as a local minimum of the signal magnitude; other criteria may be added, e.g., the magnitude is lower than a threshold. Examples for such features:

1. The number of zero-crossings within the space-dependent sample array. Low values are associated with low probe spatial variability; and
2. The number of zero-crossings within the space-dependent sample array, divided by the number of transducer elements 30 turned-on. Low values are associated with low probe spatial variability;

d. A feature associated with estimating peak widths within the space-dependent sample array, wherein the peak may be associated with one or more of the following components of the array's signal: magnitude, phase, real component, and/or imaginary component. When the space-dependent sample array is two-dimensional or multi-dimensional, said peak widths may be estimated along one or more axes of the space-dependent sample array, wherein each axis may be, but does not have to be, aligned with one of the probe's primary axes. For this purpose, one may use, for instance, the null-to-null peak width or the width of the peak at a certain level beneath the peak value (e.g., 3 dB peak width). Examples for such features:

1. A certain statistic (e.g., mean, median, predefined percentile) of the peak widths within the space-dependent sample array. High values are associated with low probe spatial variability; and
2. The width of the peak within the space-dependent sample array having the highest magnitude. High values are associated with low probe spatial variability;

e. The width of the output of the auto-correlation function applied to the space-dependent sample array. When the space-dependent sample array is two-dimensional or multi-dimensional, said width may be estimated along one or more axes of the space-dependent sample array, wherein each axis may be, but does not have to be, aligned with one of the probe's primary axes. High values are associated with low probe spatial variability; and f. A feature involving computing the power spectrum of the space-dependent sample array. When the space-dependent sample array is two-dimensional or multi-dimensional, said power spectrum may be associated with spectral analysis along one or more axes of the space-time sample array, wherein each axis may be, but does not have to be, aligned with one of the probe's primary axes. Examples for such features:

1. The energy ratio between a group of low frequency components and a group of high frequency components within the power spectrum of the space-dependent sample array. High values are associated with low probe spatial variability;
2. The energy ratio between a group of low frequency components and the total energy within the power spectrum of the space-dependent sample array. High values are associated with low probe spatial variability;
3. The energy ratio between the spectrum element with the highest energy level and the total energy within the power spectrum of the space-dependent sample array. High values are associated with low probe spatial variability;
4. The absolute frequency associated with the spectrum element with the highest energy level within the power spectrum of the space-dependent sample array. Low values are associated with low probe spatial variability; and
5. The lowest frequency associated with an element of the cumulative power spectrum of the space-dependent sample-array, whose energy is greater than (or equal to) a predefined constant (between 0 and 1) times the total energy within the power spectrum of the space-dependent sample array. Low values are associated with low probe spatial variability. The cumulative power spectrum of a signal is defined to be determined as follows:
   i. Compute the power spectrum of the signal;
   ii. For each absolute frequency, compound the power spectrum for the corresponding positive and negative frequencies, e.g., by averaging or taking the maximum over the two corresponding power spectrum elements, to obtain the "folded power spectrum"; and
   iii. For each absolute frequency, the cumulative power spectrum equals the sum of all folded power spectrum elements associated with lower or equal absolute frequencies; and ii) Let us define the "stacked space-dependent sample array" as the result of stacking the space-dependent sample arrays for multiple volume-gates, all associated with the same receive beam, in an order corresponding to the distance of the corresponding volume-gates from the probe's surface, wherein the internal order of all space-dependent sample arrays is the same. Note that when only a single volume-gate is acquired for each receive beam, for instance, when using un-coded CW transmitted signal, said stacked space-dependent sample array only includes a single volume-gate.

Let us further define a "blob" within a two-dimensional or multi-dimensional array as a continuous spatial region with no zero-crossings within it but with zero-crossings (and/or array boundaries) at its boundaries. In this context, when the two-dimensional or multi-dimensional array is real, a zero-crossing is defined as a sign change between adjacent array elements and/or the occurrence of a value being very close to 0. When the two-dimensional or multi-dimensional array is complex, a zero-crossing is defined as a local minimum of the signal magnitude; other criteria may be added, e.g., the magnitude is lower than a threshold.

Let us examine one or more components of the stacked space-dependent sample array, or a function of one or more of said components ("stacked sample-array component"), wherein the term component here refers to the magnitude, phase, real component, and/or imaginary component.

When beamforming sample alignment involves perfect focusing, a single reflector located at the center of the current volume-gate (completely clutter-free case) should result in low spatial derivative components of the stacked sample-array component along all axes, except perhaps the axis corresponding to the distance from the probe's surface, wherein the term "spatial derivative" may refer to any derivative, e.g., first or second derivative. The spatial derivative computation may be performed using any method known in the art, e.g., by convolving the signal with a spatial linear filtering kernel. An example for a one-dimensional kernel associated with first derivative computation: (−1 0 1); an example for a one-dimensional kernel associated with second derivative computation: (−½ 1 −½).

Similarly, blobs within the stacked sample-array component, associated with a single reflector located at the center of the current volume-gate, should have a long-axis which is almost perpendicular to the axis corresponding to the distance from the probe's surface.

In practical cases, physical effects such as scattering along the path of the beam, as well as the presence of multiple reflectors within volume-gates, are expected to increase:

a. The spatial derivative of the stacked sample-array component along one or more axes other than the one corresponding to the distance from the probe's surface ("stacked array spatial derivative"), wherein:
   i. The spatial derivative may be any spatial derivative, e.g., first or second derivative;
   ii. The spatial derivative may be normalized in various ways. For instance, the spatial derivative normalization may match the spatial dimensions along the applicable axis, e.g., range or cross-range axis. Alternatively, the spatial derivative normalization may match the index of the applicable axis of stacked sample-array component, e.g., the volume-gate index; and
   iii. Each axis may be, but does not have to be, aligned with one of the probe's primary axes; and
b. The absolute value of the angular difference between the orientation of the blobs within the stacked sample-array component and the orientation of a plane perpendicular to the axis corresponding to the distance from the probe's surface ("blob slope"), wherein:
   i. The blob slope may be described in terms of an angle or a spatial angle. Various coordinate systems may be employed. For example, one may employ the data acquisition coordinate system, which may be, for instance, polar, spherical or Cartesian. Another example would be to employ the indices into the stacked sample-array component; and
   ii. The blob slope may be computed for one or more axes separately, wherein each axis may be, but does not have to be, aligned with one of the probe's primary axes. Alternatively, the blob slope may be computed in multi-dimensional space, as the angle between the blob plane and the plane perpendicular to the axis corresponding to the distance from the probe's surface.

Figure 3:
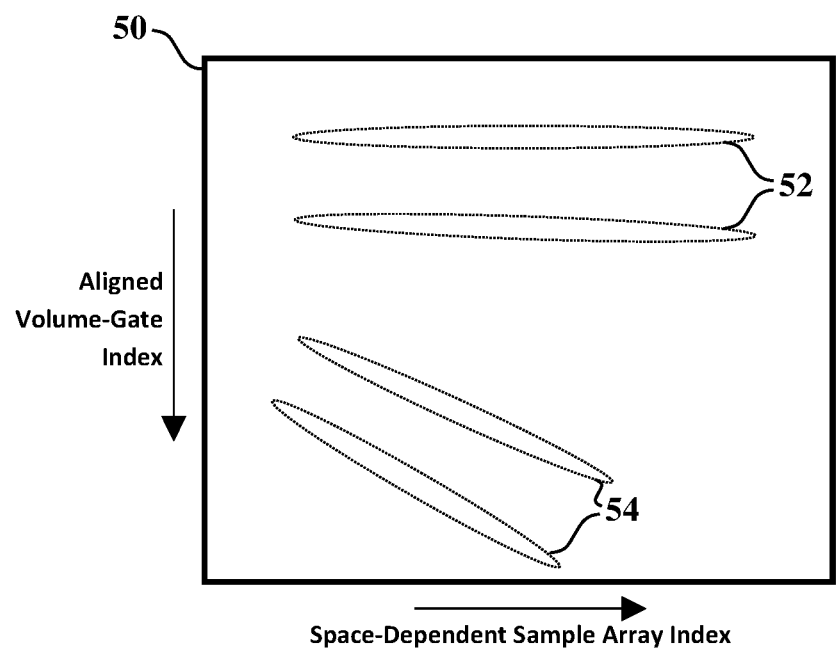
FIG. 3 is a schematic, pictorial illustration of a stacked space-dependent sample array, in accordance with an embodiment of the present invention. The horizontal axis corresponds to the index into the space-dependent sample array (e.g., when using per-channel sampling, this is the index of transducer element 30), and the vertical axis corresponds to the aligned volume-gate index (e.g., when using per-channel sampling, this is the aligned range-gate index). The boundaries of blobs associated with strong reflectors are marked by dotted ellipses. In this example, blobs 52 result from relevant reflectors, whereas blobs 54 result from clutter reflectors.
Figure 4:
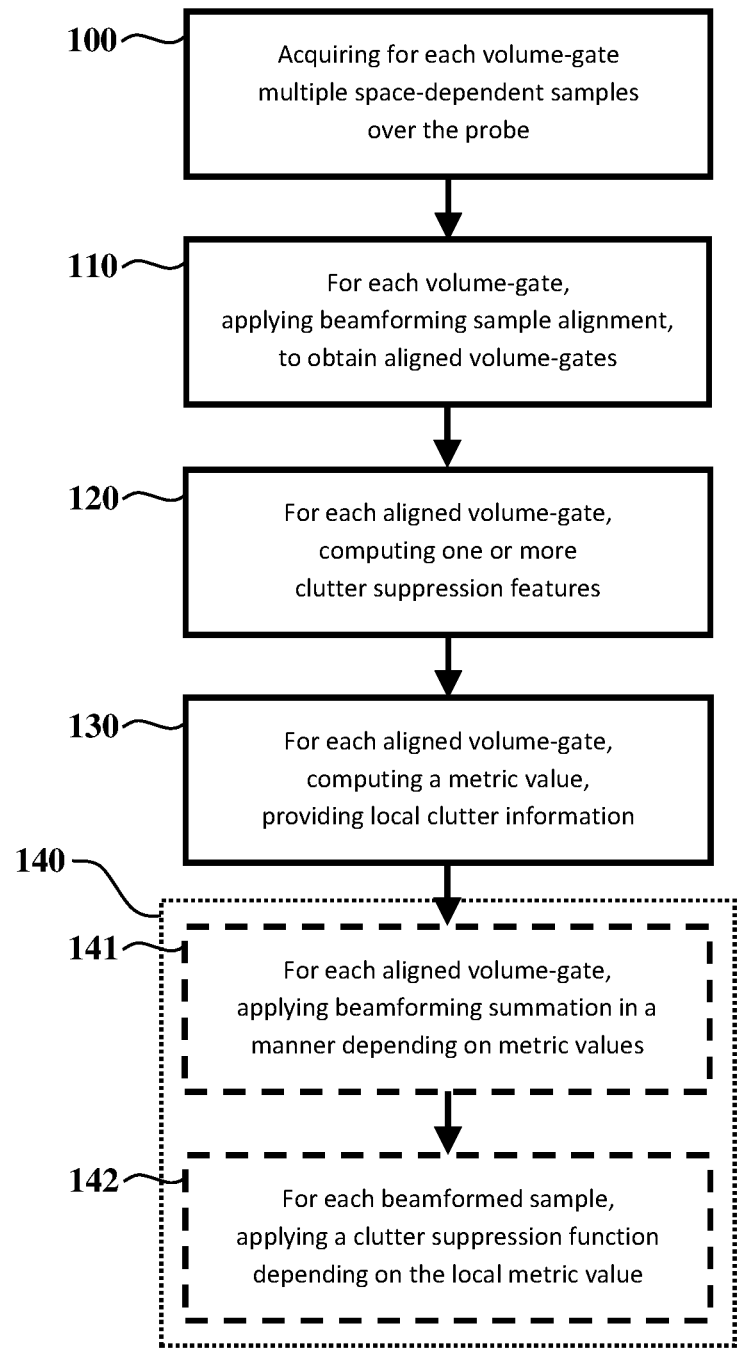
FIG. 4 is a schematic block-diagram of feature-based clutter suppression processing, in accordance with an embodiment of the present invention. The processing involves at least one of the two blocks with dashed outlines, 141 and 142.
Figure 5:
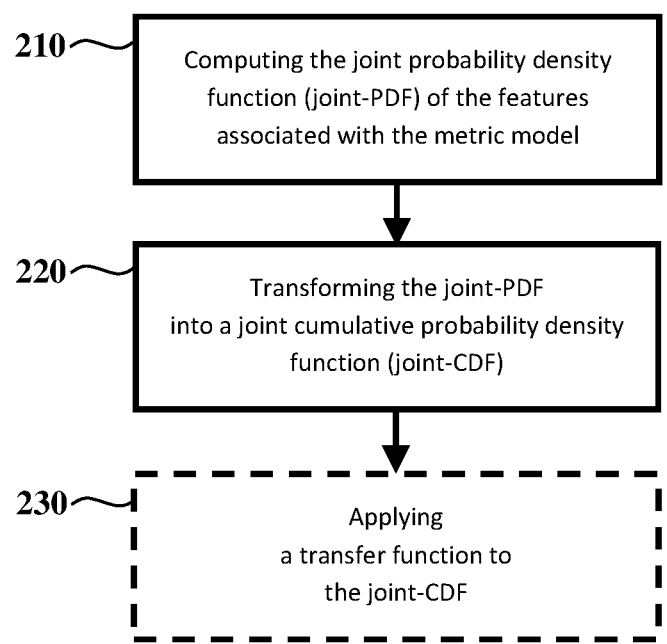
FIG. 5 is a schematic block diagram of metric model computation, in accordance with an embodiment of the present invention. The block with dashed outlines, 230, is optional.

However, the values of the stacked array spatial derivative and the blob slope are typically lower for aligned volume-gates including mostly desired information than for aligned volume-gates significantly affected by clutter. This stems from the fact that signals originating from spatial angles and/or ranges far from the center of the current volume-gate are not focused correctly in the process of beamforming sample alignment, and their beamforming phase shifts and/or time-delays are imprecise. For illustration, see FIG. 3, showing a stacked space-dependent sample array. The outlines of blobs associated with strong reflectors are marked by dotted ellipses. In this example, blobs 52 result from relevant reflectors, whereas blobs 54 result from clutter reflectors.

This assertion can be employed in one or more of the following ways:

a. Defining attributes (features) providing information regarding the local clutter level or the local probability for the aligned volume-gate to be significantly affected by clutter. Examples for such attributes, defined per volume-gate:
 1. A certain statistic (e.g., mean, weighted mean, median, certain percentile) of the local stacked array spatial derivative within the stacked space-dependent sample array and/or the stacked sample-array component;
 2. A certain statistic (e.g., mean, weighted mean, median, certain percentile) of the local blob slope within the stacked space-dependent sample array and/or the stacked sample-array component;
 3. The number of diagonal zero-crossings. A diagonal zero-crossing is defined to be detected using the following scheme:
  i. Apply zero-crossing detection to the stacked space-dependent sample array and/or the stacked sample-array component, yielding a binary matrix ("zero-crossing matrix"), where "1"s appear in zero-crossing cells, and "0" appear in all other cells;
  ii. Diagonal zero-crossings occur along diagonal lines of "1"s within the zero-crossing matrix. For two-dimensional zero-crossing matrices, this may be detected by convolving the zero-crossing matrix with a first kernel, e.g., $$\begin{pmatrix} 1 & 0 & 0 \\ 0 & 1 & 0 \\ 0 & 0 & 1 \end{pmatrix},$$

and a second kernel, e.g., $$\begin{pmatrix} 0 & 0 & 1 \\ 0 & 1 & 0 \\ 1 & 0 & 0 \end{pmatrix},$$

and identifying cells for which the convolution output for at least one of the kernels equals 1. This number increases in the presence of high blob slopes; and
 4. The number of diagonal zero-crossings, divided by the number of transducer elements 30 turned-on. This number increases in the presence of high blob slopes;

b. Blob-based direct clutter suppression processing, performed as follows:
 1. Applying blob detection within the stacked space-dependent sample array and/or the stacked sample-array component;
 2. Computing for one or more of the blobs attributes (features) associated with the stacked array spatial derivative and/or the blob slope ("blob features"); and
 3. For each blob for which blob features have been computed, adjusting all associated elements of the stacked space-dependent sample array, wherein the new value for each element of the stacked space-dependent sample array is a function ("blob function") of the original local value and of the computed blob features. For instance, the stacked space-dependent sample array signal for each blob may be multiplied by a factor depending on the stacked array spatial derivative and/or the blob slope. The multipliers for blobs with high stacked array spatial derivative and/or the blob slope should be lower than the multipliers for blobs with low stacked array spatial derivative and/or the blob slope.
  The blob function may either be predefined or an adaptively determined function of the local or regional values of the blob features.
  The blob function may also depend on other local parameters, e.g., the regional signal-to-noise ratio (SNR). The regional SNR is relevant because the computed values of the blob features may be less accurate in low-SNR regions. As a result, in low-SNR regions of the stacked space-dependent sample array, one may prefer to reduce the effect of the clutter suppression process on the array's values; and c. Local direct clutter suppression processing. This method does not necessarily involve blob detection. It adjusts some or all elements of the stacked space-dependent sample array, wherein the new value for each adjusted element of the stacked space-dependent sample array is a function ("local suppression function") of the original local value and of one or more attributes (features), indicative of the local stacked array spatial derivative and/or the local estimation of the blob slope, as computed for the stacked space-dependent sample array and/or the stacked sample-array component ("local suppression features").
  For example, when using a one-dimensional probe, the blob slope may be estimated based on the arctan of the ratio between the stacked array spatial derivative along the probe's long-axis (for a linear probe, this axis matches the cross-range) and the stacked array spatial derivative along the range axis (for instance, if the arctan of said ratio is denoted $a_r$, and $|\cdot|$ denotes the absolute operator, the blob slope may be defined as: $1-(2/\pi)\cdot||a_r|-(\pi/2)|$). As mentioned above, any spatial derivative may be employed, e.g., first or second derivative.
  When using a two-dimensional or a multi-dimensional probe, the blob slope may be similarly estimated along one or more planes, e.g., the plane defined by the range axis and horizontal axis and/or the plane defined by the range axis and the vertical axis. Additionally or alternatively, one may further transform the estimated blob slope along two or more planes into a global slope, matching the angle between the estimated blob plane and the plane perpendicular to the axis corresponding to the distance from the probe's surface.

The local suppression function may depend on each attribute indicative of the local stacked array spatial derivative and/or the blob slope (or a combination thereof) in various ways, e.g., linearly, piecewise linearly, exponentially, logarithmically, in a polynomial manner, in a sigmoid-like manner, and so forth.

The local suppression function may either be predefined or an adaptively determined function of the local or regional values of the attributes indicative of the local stacked array spatial derivative and/or the blob slope.

The local suppression function may also depend on other local parameters, e.g., the regional SNR. The regional SNR is relevant because the computed values of the local suppression features may be less accurate in low-SNR regions. As a result, in low-SNR regions of the stacked space-dependent sample array, one may prefer to reduce the effect of the clutter suppression process on the array's values.

Additionally or alternatively, the stacking of the space-dependent sample array may be performed for multiple volume-gates, corresponding to different receive beams, arranged in increasing or decreasing order of spatial angle (in one or more axes) and/or in increasing or decreasing order of cine-loop frame index. A processing similar to the one described above can be employed in such cases.

Feature-Based Clutter Suppression Processing

Clutter Suppression Scheme

In embodiments of the present invention, the processing of the acquired data comprises:

i) Step 110: For one or more volume-gates, applying beamforming sample alignment (includes applying the phase shifts and/or time-delays to the samples, associated with beamforming), to obtain one or more aligned volume-gates;

ii) Step 120: For each of the one or more aligned volume-gates, computing one or more clutter suppression features, wherein a clutter suppression feature provides information which is indicative, either by itself or when combined with other clutter suppression features, of the local clutter level or the probability for the aligned volume-gate to be significantly affected by clutter;

iii) Step 130: For each of the one or more aligned volume-gates, computing a metric value, indicative of the local clutter level within the aligned volume-gate or the probability for the aligned volume-gate to be significantly affected by clutter, wherein the metric value depends on values of one or more of the one or more clutter suppression features for the aligned volume-gate, and possibly for additional aligned volume-gates; and iv) Step 140: Performing one or more of the following:
a. Step 141: For one or more of the one or more aligned volume-gates, applying beamforming summation in a manner depending on the metric value for the corresponding aligned volume-gate, and possibly also on the metric value for additional aligned volume-gates ("adaptive beamforming summation"); and b. Step 142: For one or more beamformed samples, each of which is associated with one of the one or more aligned volume-gates, applying a clutter suppression function to the beamformed sample value, wherein the clutter suppression function is a function depending on the metric value for the corresponding aligned volume-gate, and possibly also on the metric value for additional aligned volume-gates.

In some embodiments of step 110, wherein per-channel sampling or sampling per sub-array is employed, the aligned volume-gates are equivalent to aligned range-gates.

In further embodiments of step 110, each volume-gate may be used to generate one or more aligned volume-gate. For example, when using per-channel sampling or sampling per sub-array, the acquired data for each volume-gate may be used in one or more concurrent receive beams, and different receive beams may use different phase-shifts and/or time delays.

In certain embodiments of step 110, the beamforming sample alignment is only associated with beamforming on reception.

In other embodiments of step 110, when two-way beamforming by processing is used (for instance, when orthogonal sub-array coded excitation is employed), the beamforming sample alignment may be associated with one of:
i) Beamforming on reception only; and
ii) Beamforming on both transmission and reception.

In further embodiments, when two-way beamforming by processing is used (for instance, when orthogonal sub-array coded excitation is employed), step 110 may further comprise applying beamforming summation, associated with beamforming on transmission.

In some embodiments, step 140 further comprises applying a transfer function to the outputs of step 141 and/or step 142 ("output transfer function").

Clutter Suppression Feature Computation (Step 120)

In embodiments of step 120, at least one of the clutter suppression features is derived from one or more of the desired information characteristics.

In further embodiments of step 120, at least one of the clutter suppression features is one of:

i) A feature derived for each aligned volume-gate from the space-dependent sample array, in one of the following ways:
a. The standard deviation or variance of the space-dependent sample array, taking into account one or more of the following components of the array's signal: magnitude, phase, real component, and/or imaginary component;
b. A certain statistic (e.g., mean, median, predefined percentile) of the spatial derivatives within the space-dependent sample array, taking into account one or more of the following components of the array's signal: magnitude, phase, real component, and/or imaginary component. The term "spatial derivative" here may refer to any derivative, e.g., first or second derivative. When the space-dependent sample array is two-dimensional or multi-dimensional, said spatial derivatives may be in one or more axes of the space-dependent sample array, wherein each axis may be, but does not have to be, aligned with one of the probe's primary axes;
c. A feature associated with counting zero-crossings within the space-dependent sample array. When the space-dependent sample array is real, a zero-crossing is defined as a sign change between adjacent array elements and/or the occurrence of a value being very close to 0. When the space-dependent sample array is complex, a zero-crossing is defined as a local minimum of the signal magnitude; other criteria may be added, e.g., the magnitude is lower than a threshold. Examples for such features:
1. The number of zero-crossings within the space-dependent sample array; and
2. The number of zero-crossings within the space-dependent sample array, divided by the number of transducer elements 30 turned-on;

d. A feature associated with estimating peak widths within the space-dependent sample array, wherein the peak may be associated with one or more of the following components of the array's signal: magnitude, phase, real component, and/or imaginary component. When the space-dependent sample array is two-dimensional or multi-dimensional, said peak widths may be estimated along one or more axes of the space-dependent sample array, wherein each axis may be, but does not have to be, aligned with one of the probe's primary axes. For this purpose, one may use, for instance, the null-to-null peak width or the width of the peak at a certain level beneath the peak value (e.g., 3 dB peak width). Examples for such features:
1. A certain statistic (e.g., mean, median, predefined percentile) of the peak widths within the space-dependent sample array; and
2. The width of the peak within the space-dependent sample array having the highest magnitude;

e. The width of the output of the auto-correlation function applied to the space-dependent sample array. When the space-dependent sample array is two-dimensional or multi-dimensional, said width may be estimated along one or more axes of the space-dependent sample array, wherein each axis may be, but does not have to be, aligned with one of the probe's primary axes;

f. A feature involving computing the power spectrum of the space-dependent sample array. When the space-dependent sample array is two-dimensional or multi-dimensional, said power spectrum may be associated with spectral analysis along one or more axes of the space-time sample array, wherein each axis may be, but does not have to be, aligned with one of the probe's primary axes. Examples for such features:
1. The energy ratio between a group of low frequency components and a group of high frequency components within the power spectrum of the space-dependent sample array;
2. The energy ratio between a group of low frequency components and the total energy within the power spectrum of the space-dependent sample array;
3. The energy ratio between the spectrum element with the highest energy level and the total energy within the power spectrum of the space-dependent sample array;
4. The absolute frequency associated with the spectrum element with the highest energy level within the power spectrum of the space-dependent sample array; and
5. The lowest frequency associated with an element of the cumulative power spectrum of the space-dependent sample-array, whose energy is greater than (or equal to) a predefined constant (between 0 and 1) times the total energy within the power spectrum of the space-dependent sample array; and g. A function of one of more of (a)-(f) above; and ii) A feature derived for each aligned volume-gate from the corresponding cells of the stacked space-dependent sample array, in one of the following ways:
a. A certain statistic (e.g., mean, weighted mean, median, certain percentile) of the local stacked array spatial derivative within the stacked space-dependent sample array and/or the stacked sample-array component;
b. A certain statistic (e.g., mean, weighted mean, median, certain percentile) of the local blob slope within the stacked space-dependent sample array and/or the stacked sample-array component;
c. The number of diagonal zero-crossings;
d. The number of diagonal zero-crossings, divided by the number of transducer elements 30 turned on; and
e. A function of one or more of the outputs of (a)-(d) above.

In some embodiments, step 120 further comprises applying a correction to the computed values of the clutter suppression features ("feature correction", e.g., multiplying each computed value by a correction factor), wherein the correction for each aligned volume-gate depends on one or more of the following:
i) The spatial angle between the boresight of the transmit beam and the boresight of the receive beam. Such corrections are applicable, for instance, in systems employing MLA;
ii) The spatial angle between the receive beam's boresight and the broadside. Such corrections are applicable, for instance, in phased-array probes, performing digital beam steering; and
iii) The sample's distance from the probe's surface, measured along the path of the beam. Such corrections are based on a model for medium related effects within the target region.

For example, for clutter suppression features whose value is linearly correlated to the local width of the mainlobe, the feature correction may involve multiplying the computed value of said clutter suppression features by the cosine of the local spatial angle between the beam's boresight and the broadside, thus compensating for the broadening of the beam mainlobe due to beam steering.

Metric Value Computation (Step 130)

In certain embodiments of step 130, the metric value is one of:
i) Indicative of the probability for the corresponding aligned volume-gate to be substantially affected by clutter effects only, i.e., essentially all its received energy originates from clutter effects;
ii) Indicative of the probability for the corresponding aligned volume-gate to be substantially unaffected by clutter effects;
iii) Indicative of the percentage of the received energy within the corresponding aligned volume-gate that originates from clutter effects;
iv) Indicative of the percentage of the received energy within the corresponding aligned volume-gate that originates from relevant information; and
v) Set to a certain constant, e.g., 0.0, if the corresponding aligned volume-gate is not significantly affected by clutter effects, and otherwise to a different constant, e.g., 1.0.

In some embodiments of step 130, the metric value only depends on the values of clutter suppression features for the corresponding aligned volume-gate. In other embodiments of step 130, the metric value depends on the values of clutter suppression features for both the corresponding aligned volume-gate and additional aligned volume-gates, which may be at least one of: (i) spatially adjacent, either limiting the scope of the term "spatially adjacent" to one or more axes or in any axis; and (ii) temporally adjacent, e.g., associated with an adjacent frame.

In some embodiments of step 130, the metric value is a predefined function of the local values of one or more clutter suppression features. For example, the predefined function may be a linear function of the values of the one or more clutter suppression features. Another possible predefined function may be the result of multiplying linear functions of each of the one or more clutter suppression features.

In other embodiments of step 130, the metric value is an adaptively determined function of the local or regional values of one or more clutter suppression features. Adaptively determined functions may be used to cope with medium related physical phenomena along the path of the beam, affecting the local distribution of clutter suppression feature values, even for aligned volume-gates including mostly desired information.

In certain embodiments of step 130, the following assumptions are employed for the adaptively determined function:
  i) If the signal for an aligned volume-gate can be associated with a single dominant reflector, and the clutter suppression features are defined in accordance with the desired information characteristics, the values of the computed clutter suppression features for that aligned volume-gate are expected to depend on the spatial angle between the single dominant reflector and the beam's boresight (this assumption is referred to as the "spatial angle dependence assumption");
  ii) The prevalence of a set of values for the clutter suppression features, associated with a certain spatial angle with respect to the beam's boresight, is correlated to the beam gain at that spatial angle (this assumption is referred to as the "prevalence assumption"). If the spatial angle dependence assumption is correct, the prevalence assumption is precise when the medium within the target region is approximately homogeneous.

Additionally or alternatively, one can employ the following assumption:
  i) By definition, clutter suppression features provide information which is indicative of the local clutter level or the probability for an aligned volume-gate to be significantly affected by clutter. For each feature, one may theoretically determine whether the desired metric value (associated with the estimation of the local clutter level or the probability for the aligned volume-gate to be significantly affected by clutter) is expected to either increase or decrease with one of: (a) the feature value; or (b) a function of the feature value, e.g., the absolute value of the feature value (this assumption is referred to as the "feature trend assumption").

Given the above assumptions, the adaptively determined function for a given spatial and/or temporal region may be based on spatial and/or temporal analysis of the values of the clutter suppression features within the spatial and/or temporal region. Accordingly, in certain embodiments of step 130, computing the metric value comprises:

i) Computing one or more metric models, wherein each metric model is associated with a group of aligned volume-gates ("aligned volume-gate group") and one or more of the one or more clutter suppression features ("feature group"). The aligned volume-gate group may include all aligned volume gates, in all frames. Alternatively, the aligned volume-gates may be divided into aligned volume-gate groups in accordance with one or more of the following:
   a. Swaths of range with respect to the probe's surface;
   b. Swaths of beam phase center over the probe's surface;
   c. Swaths of spatial angle between the receive beam's boresight and broadside;
   d. Swaths of spatial angle between the boresights of the transmit beam and the receive beam; and
   e. Time swaths, e.g., defined as a certain number of consecutive frames.
   Note that an aligned volume-gate group may be associated with more than one swath of the above mentioned parameters. For instance, in 2D scanning, an aligned volume-gate group may be associated with all beams for which the absolute value of the receive beam's azimuth angle is between a predefined minimal and a predefined maximal value (in this case, the aligned volume-gate group includes two separate spatial angle swaths);
  ii) For each of the one or more aligned volume-gates, setting the local metric value in accordance with the value of one or more metric models, associated with the local value of the clutter suppression features.
   In certain embodiments, when more than one aligned volume-gate group is defined, the local metric value may be based on one of the following:
   a. The metric models associated with the current aligned volume-gate group; or
   b. The metric models associated with the current aligned volume-gate group and one or more spatially and/or temporally adjacent aligned volume-gate groups. For example, one may associate each model with the spatial and/or temporal center-of-mass of the aligned volume-gate group, and for each aligned volume-gate employ interpolation between the values for the different models, in accordance with the spatial location of the aligned volume-gate with respect to said centers-of-mass.

Figure 6:
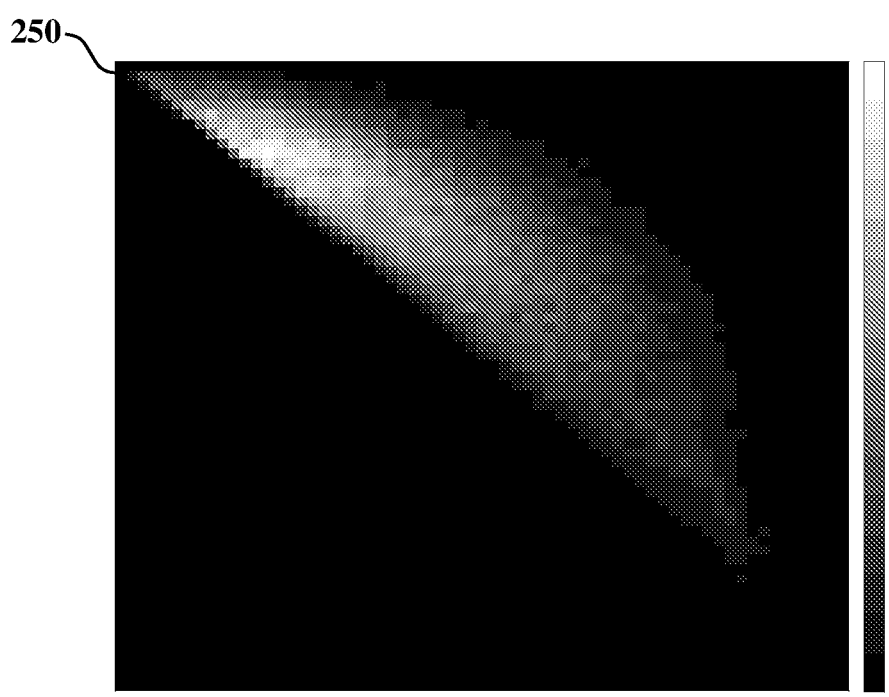
FIG. 6 is a schematic, pictorial illustration of an example for an output of step 210, the joint probability density function (joint-PDF) of two clutter suppression features associated with a metric model, in accordance with an embodiment of the present invention. The horizontal and vertical axes correspond to the values of the two features, and the local gray-level is indicative of the joint-PDF value for each pair of feature values.

In some embodiments of step 130, computing a metric model for an aligned volume-gate group comprises:
  i) Step 210: Computing the joint probability density function (joint-PDF) of the feature group associated with the metric model, taking into account only volume-gates associated with the volume-gate group associated with the metric model.
   The joint-PDF can be implemented, for instance, by computing a joint-histogram, and normalizing the histogram so that the sum of all its values would equal 1.0. The range of values for each axis of the joint-histogram may be predetermined or adaptively determined based on the computed range of values for the corresponding clutter suppression feature. The set of bins employed for each axis of the joint-histogram may be equally spaced or non-uniformly determined. An example for the output of step 210 for a feature group with two features can be seen in FIG. 6; and
  ii) Step 220: Transforming the joint-PDF into a joint cumulative probability density function (joint-CDF).

The joint-CDF may use the same set of bins for each axis as the joint-PDF. The values of the joint-CDF typically range from 0.0 to 1.0. The joint-CDF computation may be performed in one of the following ways:

a. Each element of the joint-CDF equals the sum of the values of all joint-PDF elements whose value is one of: (1) equal to or higher than the joint-PDF value for the current element; (2) equal to or lower than the joint-PDF value for the current element; (3) higher than the joint-PDF value for the current element; and (4) lower than the joint-PDF value for the current element. For options (1) and (3), the joint-CDF value increases with the local clutter level or the probability for the aligned volume-gate to be significantly affected by clutter. For options (2) and (4), the joint-CDF value decreases with the local clutter level or the probability for the aligned volume-gate to be significantly affected by clutter.

This method may be explained by the prevalence assumption; and b. Each element of the joint-CDF equals the sum of the values of all joint-PDF elements associated with feature group values corresponding to one of: (1) equal or higher clutter level or probability for an aligned volume-gate to be significantly affected by clutter; (2) equal or lower clutter level or probability for an aligned volume-gate to be significantly affected by clutter; (3) higher clutter level or probability for an aligned volume-gate to be significantly affected by clutter; and (4) lower clutter level or probability for an aligned volume-gate to be significantly affected by clutter.

This method may be explained by a combination of the prevalence assumption and the feature trend assumption.

For instance, if the feature group includes two features, wherein the value of each of said features increases with the estimated local clutter level, and we define that the metric value increases with the local clutter level, each element of the joint-CDF should equal the sum of the values of all elements of the joint-PDF that correspond to lower (and optionally equal) values for each of the features in the feature group. If, for instance, we sum over joint-PDF elements corresponding to lower and equal values for each of the features, the summation can be defined by eq. (7):

$$P(a,b)=\sum_{n=1}^{a}\sum_{m=1}^{b}p(n,m) \quad (7)$$

Wherein p is the joint-PDF and P is the joint-CDF, both of which are given as functions of the bin index for the first and second clutter suppression features in the feature group.

Figure 7:
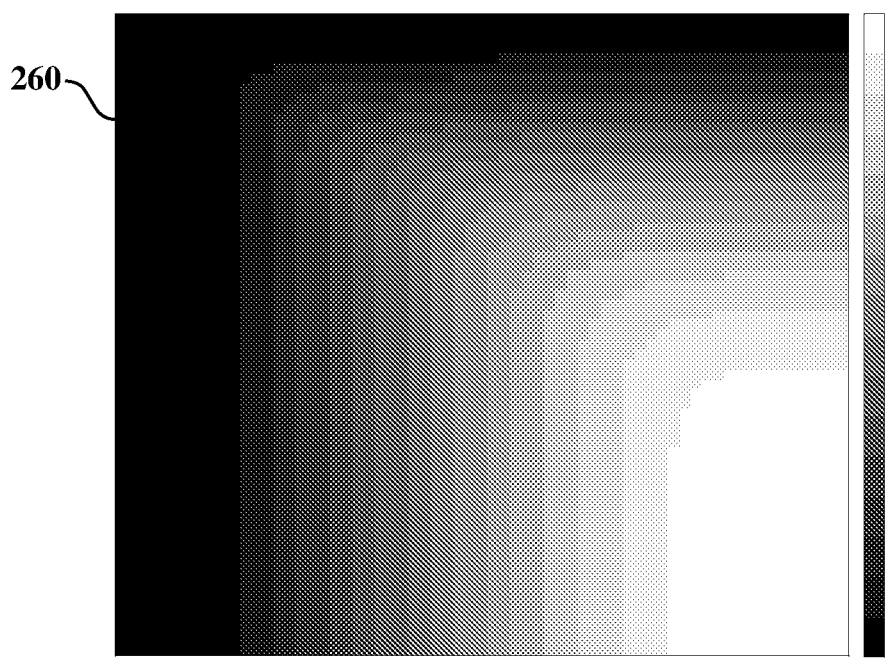
FIG. 7 is a schematic, pictorial illustration of an example for an output of step 220, the joint cumulative probability density function (joint-CDF) of two clutter suppression features associated with a metric model, in accordance with an embodiment of the present invention. The horizontal and vertical axes correspond to the values of the two features, and the local gray-level is indicative of the joint-CDF value for each pair of feature values.

An example for the output of step 220 for a feature group with two features can be seen in FIG. 7.

The output of step 220 is a metric model, that is, a matrix defining the metric value for each set of values of the feature group, over a grid defined by the joint-CDF bins. When determining the local metric value for an aligned volume-gate, based on the corresponding values for the feature group and a given metric model, one can either employ interpolation or use the nearest neighbor within the metric model.

In certain embodiments of step 130, computing the metric model for an aligned volume-gate group further comprises step 230: applying a transfer function to the joint-CDF, to obtain an adapted metric model, to be employed for metric value computation.

Figure 8:
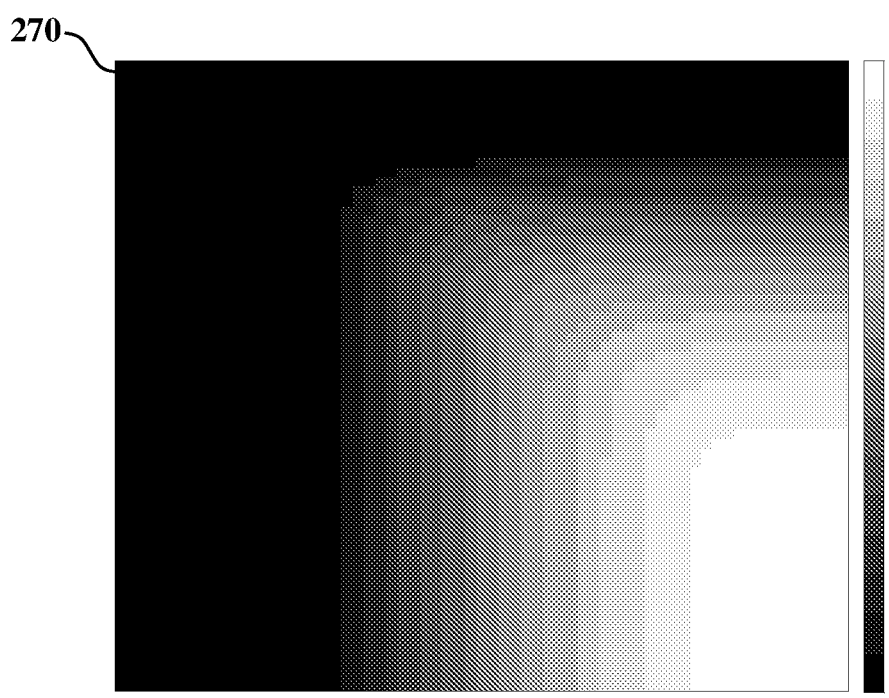
FIG. 8 is a schematic, pictorial illustration of an example for an output of step 230, the adapted metric model for two clutter suppression features, after applying an adaptive stretching transfer function to the joint-CDF, in accordance with an embodiment of the present invention. The horizontal and vertical axes correspond to the values of the two features, and the local gray-level is indicative of the metric model value for each pair of feature values.
Figure 9:
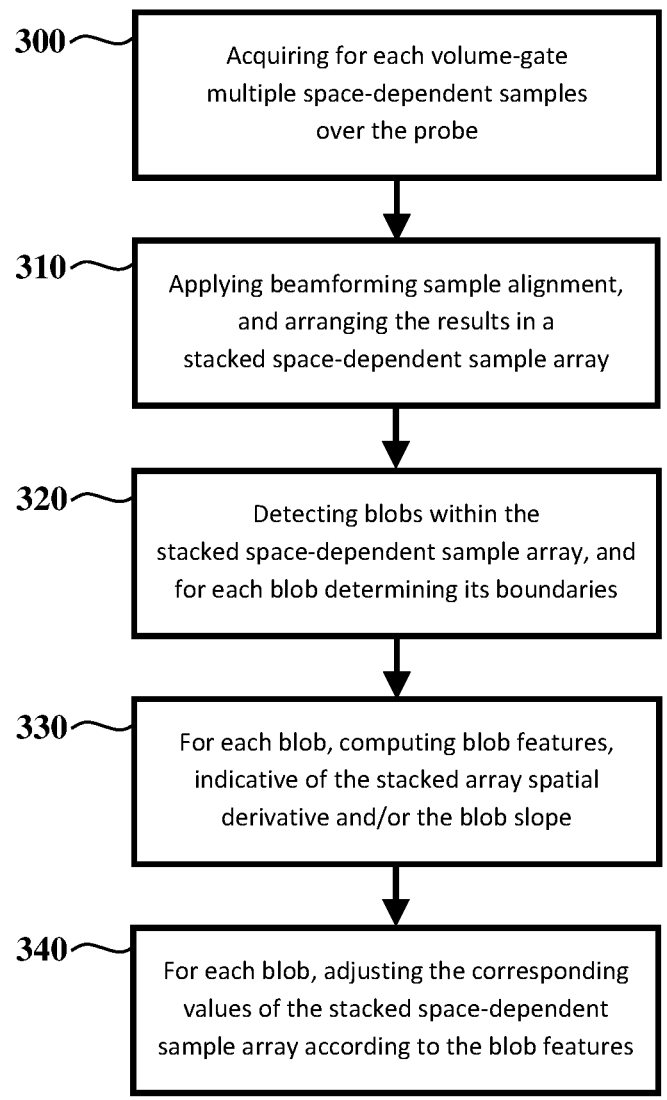
FIG. 9 is a schematic block-diagram of blob-based direct clutter suppression processing, in accordance with an embodiment of the present invention.
Figure 10:
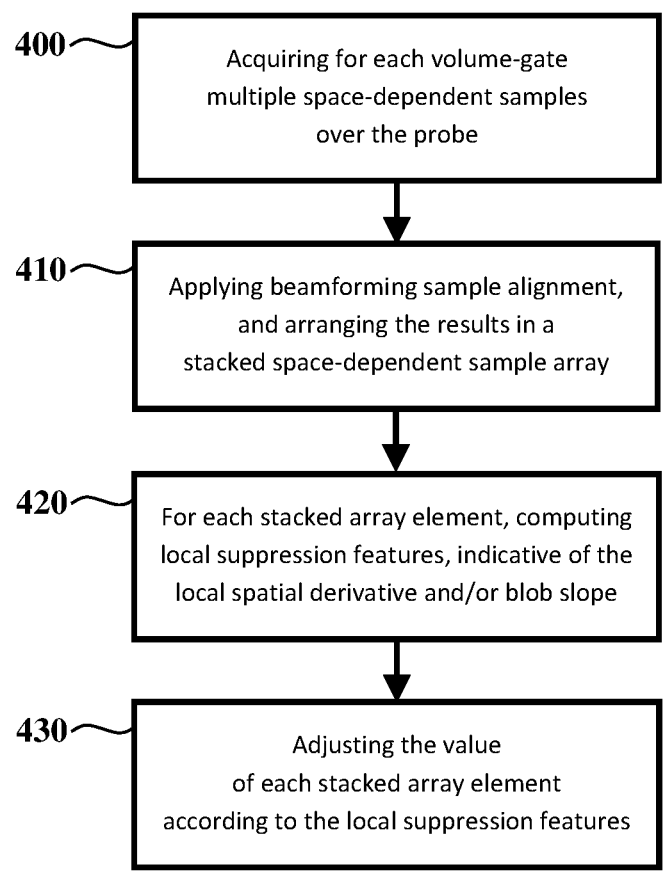
FIG. 10 is a schematic block-diagram of local direct clutter suppression processing, in accordance with an embodiment of the present invention.

In some embodiments of step 230, the transfer function is predetermined, whereas in other embodiments the transfer function is adaptive. An example for the output of step 230 for a feature group with two features, after applying an adaptive stretching transfer function to the joint-CDF, can be seen in FIG. 8.

In embodiments of step 230, the adaptive transfer function makes use of one or more of the following parameters, derived from the joint-PDF and/or the joint-CDF (i.e., the metric model):

i) The clutter suppression feature values associated with the joint-PDF peak, defined as one of: (a) the element within the joint-PDF whose value is highest; (b) the center-of-mass of the joint-PDF; or (c) the center-of-mass of the joint-PDF, after discarding all joint-PDF distribution modes other than the one with the highest peak and/or highest total probability.

The joint-PDF peak corresponds to the most ubiquitous set of values for the feature group. According to the prevalence assumption, this set of values is expected to correspond to essentially clutter-free aligned volume-gates;

ii) The clutter suppression feature values associated with the joint-PDF positive extended peak, wherein the following definitions are employed:

a. The "long-axis of the joint-PDF" is a unit vector within the joint-PDF, pointing at the direction along which the joint-CDF value grows most rapidly with respect to the joint-PDF peak. Note that, if the feature group includes a single clutter suppression feature, the joint-PDF is one-dimensional, and the long-axis of the joint-PDF coincides with the axis of said one dimension; and b. The "joint-PDF positive extended peak" is the element within the joint-PDF, found when starting at the joint-PDF peak and following the direction of the long-axis of the joint-PDF, until reaching an element of the joint-PDF whose value is equal to or lower than the highest joint-PDF value, multiplied by a predefined factor between 0.0 and 1.0, e.g., 0.5. If such a value is not found before reaching the joint-PDF periphery, the applicable joint-PDF element along the boundaries is employed; and iii) The clutter suppression feature values associated with the joint-PDF negative extended peak, wherein the following definitions are employed:

a. The "joint-PDF negative extended peak" is the element within the joint-PDF, found when starting at the joint-PDF peak and following the direction opposite to the long-axis of the joint-PDF, until reaching an element of the joint-PDF whose value is equal to or lower than the highest joint-PDF value, multiplied by a predefined factor between 0.0 and 1.0, e.g., 0.5. If such a value is not found before reaching the joint-PDF periphery, the applicable joint-PDF element along the boundaries is employed.

In further embodiments of step 230, the adaptive transfer function involves one or more of the following, in any order:

i) Setting all metric model elements whose value is lower than (and optionally equal to) an adaptively determined value to a certain value, e.g., the metric model value at the joint-PDF peak, wherein the adaptively determined value is one of:

a. The metric model value at the joint-PDF peak;
b. The metric model value at the joint-PDF positive extended peak, with a certain predefined factor; and
c. The metric model value at the joint-PDF negative extended peak, with a certain predefined factor;

ii) Setting all metric model elements whose value is higher than (and optionally equal to) an adaptively determined value to a certain value, e.g., the metric model value at the joint-PDF peak, wherein the adaptively determined value is one of:
a. The metric model value at the joint-PDF peak;
b. The metric model value at the joint-PDF positive extended peak, with a certain predefined factor; and
c. The metric model value at the joint-PDF negative extended peak, with a certain predefined factor;

iii) Linearly stretching the metric model values between a first boundary and a second boundary, wherein each of the first and second boundary is one of the following:
a. The metric model value at the joint-PDF peak;
b. The metric model value at the joint-PDF positive extended peak, with a certain predefined factor;
c. The metric model value at the joint-PDF negative extended peak, with a certain predefined factor;
d. The minimal metric model value;
e. The maximal metric model value; and
f. A predefined constant, e.g., 0 or 1.

Wherein the stretching may be described by eq. (8):

$$M_{out} = \begin{cases} 0 & \text{if } M_{in} \leq M_{min} \\ 1 & \text{if } M_{in} \geq M_{max} \\ \frac{M_{in} - M_{min}}{M_{max} - M_{min}} & \text{if } M_{max} > M_{in} > M_{min} \end{cases} \quad (8)$$

wherein $M_{in}$ is the input to the transfer function, $M_{out}$ is the output of the transfer function, $M_{min}$ is the first boundary and $M_{max}$ is the second boundary; and iv) Applying to the metric model values one of:
a. A polynomial function, e.g., parabolic function;
b. An exponential function; and
c. A logarithmic function.

In even further embodiments of step 230, the application of the transfer function is incorporated with the joint-CDF computation.

Adaptive Beamforming (Step 141)

In embodiments of step 141, the adaptive beamforming summation is applied to the aligned volume-gates either before, during or after applying matched filtering.

In some embodiments of step 141, the adaptive beamforming summation only depends on the metric value for the corresponding aligned volume-gate. In other embodiments of step 141, the adaptive beamforming summation depends on the metric value for both the corresponding aligned volume-gate and additional aligned volume-gates, which may be at least one of: (i) spatially adjacent, either limiting the scope of the term "spatially adjacent" to one or more axes or in any axis; and (ii) temporally adjacent, e.g., associated with an adjacent frame.

In some embodiments, the adaptive beamforming summation for each aligned volume-gate depends on the result of applying a spatial low-pass filter to the metric values associated with the corresponding aligned volume-gate and spatially adjacent aligned volume-gates, associated with the same receive beam. The low-pass filter may be linear (e.g., using weighted averaging) or non-linear (e.g., using the minimum or maximum operator). This is useful, for example, when the metric values are computed based on clutter suppression features derived from real matched-filtered signal, in which case the local metric values may be affected by spatial variations associated with phase changes within the signal envelope. In such cases, the number of spatially adjacent metric values to which the low-pass filter is applied may be set so as to match the ratio between the sampling frequency on reception and the transmitted carrier frequency (i.e., the number of samples per carrier wavelength).

In certain embodiments of step 141, the adaptive beamforming summation comprises adaptively determining one or more of the following beamforming summation parameters depending on the metric value for the corresponding aligned volume-gate, and possibly also on the metric value for additional aligned volume-gates:

i) The set of transducers 30 turned-on for the corresponding aligned volume-gate;
ii) The apodization pattern employed for the corresponding aligned volume-gate. For instance, when the local metric value is indicative of relatively high clutter level within the aligned volume gate or relatively high probability for the aligned volume-gate to be significantly affected by clutter, one can use apodization patterns yielding lower sidelobe levels (and therefore reduced sidelobe clutter effects) than in other cases; and
iii) A multiplier applied to all samples associated with the corresponding aligned volume-gate ("global multiplier"). For example, the global multiplier may be set so as to compensate for signal-to-noise ratio reduction due to using the selected apodization pattern for the corresponding aligned volume-gate. Additionally or alternatively, the global multiplier may be a function of the metric value for the corresponding aligned volume-gate, e.g., a linear function.

Clutter Suppression Function Application (Step 142)

In embodiments of step 142, the clutter suppression function is applied to the beamformed sample value either before, during or after applying matched filtering.

Furthermore, the clutter suppression function may be applied before or after any of the additional processing applied on reception, as described herein above. For instance, the clutter suppression function may be applied before or after applying log-compression.

In some embodiments of step 142, the clutter suppression function only depends on the metric value for the corresponding aligned volume-gate. For example, the clutter suppression function may simply multiply the beamformed sample value by the metric value for the corresponding aligned volume-gate.

In other embodiments of step 142, the clutter suppression function depends on the metric value for both the corresponding aligned volume-gate and additional aligned volume-gates, which may be at least one of: (i) spatially adjacent, either limiting the scope of the term "spatially adjacent" to one or more axes or in any axis; and (ii) temporally adjacent, e.g., associated with an adjacent frame.

In some embodiments, the clutter suppression function depends on the result of applying a spatial low-pass filter to the metric values associated with the corresponding aligned volume-gate and spatially adjacent aligned volume-gates, associated with the same receive beam. The low-pass filter may be linear (e.g., using weighted averaging) or non-linear (e.g., using the minimum or maximum operator). This is useful, for example, when the metric values are computed based on clutter suppression features derived from real matched-filtered signal, in which case the local metric values may be affected by spatial variations associated with phase changes within the signal envelope. In such cases, the number of spatially adjacent metric values to which the low-pass filter is applied may be set so as to match the ratio between the sampling frequency on reception and the transmitted carrier frequency (i.e., the number of samples per carrier wavelength).

Output Transfer Function (Step 140)

In embodiments of step 140, the output transfer function is predetermined, whereas in other embodiments the output transfer function is adaptive.

In some embodiments of step 140, the adaptive output transfer function involves one or more of the following, in any order:
i) Applying one of:
   a. A polynomial function, e.g., a linear or a parabolic function;
   b. An exponential function; and
   c. A logarithmic function; and
ii) Applying a linear function, depending on the metric value for the corresponding aligned volume-gate, and possibly also on the metric value for additional aligned volume-gates depending.

In further embodiments of step 140, the adaptive output transfer function makes use of one or more of the following parameters, derived from the joint-PDF and/or the joint-CDF (i.e., the metric model):
i) The clutter suppression feature values associated with the joint-PDF peak;
ii) The clutter suppression feature values associated with the joint-PDF positive extended peak, with a certain predefined factor; and
iii) The clutter suppression feature values associated with the joint-PDF negative extended peak, with a certain predefined factor.

EXAMPLE

As an example of an ultrasound apparatus to perform the method, the probe has a one-dimensional transducer array, and per-channel sampling is employed. In the example method, for each receive beam or group or receive beams, for each volume-gate, beamforming sample alignment is applied. Then for each aligned volume-gate, a single clutter suppression feature is computed, in this example the ratio between the number of zero-crossings within the space-dependent sample array and the number of elements turned-on within the space-dependent sample array. That the ratio between the number of zero-crossings and the number of elements turned-on is indicative of the local clutter level can be seen, for example, with reference to FIG. 3. The vertical axis corresponds to the aligned volume-gate index, so each aligned volume-gate corresponds to a row in the figure. A perfectly focused reflector at the center of the beam is expected to produce a horizontal blob (as in 52). In such cases, a single blob is expected to pass through the row. The boundaries of each blob are defined by zero-crossings, so the number of zero-crossings should be relatively small. Conversely, regions with clutter reflectors are expected to produce slanted blobs (as in 54). As a result, multiple blobs would pass through each row, increasing the number of zero-crossings and thus indicating a greater likelihood of clutter. The number of zero-crossings is divided by the number of elements turned-on, because in any given scenario, a smaller number of elements turned-on reduces the expected number of zero-crossings.

In this example, for each aligned volume-gate, a metric value is computed, using a metric model computed for all aligned volume-gates within the frame. The metric model is computed in the following manner. The PDF of the values of the clutter suppression feature is computed using all aligned volume-gates of all receive beams associated with the current frame, by the use of histogram computation, where each bin is associated with a range of clutter suppression feature values. The PDF is transformed into a CDF using cumulative summation, and a transfer function is applied to the CDF as follows. The element index within the PDF corresponding to the highest PDF value is determined, and the CDF value corresponding to the found element index is determined. A linear transfer function is applied to the CDF, transforming the found CDF value to 0, and transforming 1 to 1. All updated CDF values lower than 0 are then set to 0. Note that, given a specific clutter suppression feature value, one may determine the metric model value using interpolation over the metric model. For each aligned volume-gate, beamforming summation is applied, and the output is multiplied by 1 minus the local metric value. In this way, each aligned volume-gate associated with highly-variable values in the space-dependent sample array receive a high metric value, and are then suppressed or cancelled during beamforming summation.

Blob-Based Direct Clutter Suppression Processing

In embodiments of the present invention, the processing of the acquired data comprises:
i) Step 310: For one or more volume-gates, applying beamforming sample alignment (includes applying the phase-shifts and/or time delays to the samples, associated with beamforming), and arranging the results in a stacked space-dependent sample array;
ii) Step 320: Detecting one or more blobs within the stacked space-dependent sample array, and for each such blob determining its boundaries;
iii) Step 330: For at least one of the one or more blobs, computing one or more blob features, wherein a blob feature is indicative of at least one of: (a) the stacked array spatial derivative in one or more axes; and (b) the blob slope in one or more axes; and
iv) Step 340: For each blob for which blob features have been computed, applying a function to the values of the stacked space-dependent sample array elements associated with the blob ("blob function"), wherein the blob function depends on the values of the corresponding blob features.

In certain embodiments of step 320, detecting one or more blobs and determining their boundaries is performed either directly on the stacked space-dependent sample array, or using one or more of the following components of the array's signal: magnitude, phase, real component, and/or imaginary component.

In some embodiments of step 320, detecting one or more blobs and determining their boundaries is performed using segmentation methods known in the art. For instance, one may detect a high magnitude element of the stacked space-dependent sample array, and employ region-growing methodologies to detect its boundaries, wherein a boundary is met where a zero-crossing occurs.

In embodiments of step 340, the blob function may either be predefined or an adaptively determined function of the local or regional values of the blob features.

In certain embodiments of step 340, for each element of the stacked space-dependent sample array within the blob, the blob function output only depends on the value of said element and the values of the corresponding blob features.

For instance, the blob function may involve multiplying each element of the stacked space-dependent sample array within the blob by a factor between 0.0 and 1.0, wherein the factor is a function of the corresponding values of the blob features.

In other embodiments of step 340, for each element of the stacked space-dependent sample array within the blob, the blob function output depends on the values of the stacked space-dependent sample array for said element and elements in its spatial and/or temporal vicinity, as well as on the values of the corresponding blob features. For example, in cases where the values of the blob features indicate significant clutter effect, one may replace the stacked space-dependent sample array values within the blob by values matching adjacent elements, using spatial and/or temporal interpolation.

In certain embodiments of step 340, the blob function may depend on each blob feature (or combination of features) in various ways, e.g., linearly, piecewise linearly, exponentially, logarithmically, in a polynomial manner, in a sigmoid-like manner, and so forth.

In further embodiments of step 340, the blob function may depend on the average, on the weighted average, or on a certain percentile (e.g., minimum or maximum value) of the local values of the local suppression features. Any type of averaging known in the art may be employed, e.g., arithmetic mean, geometric mean, median and so on.

In even further embodiments of step 340, the blob function also depends on other local parameters, such as the regional SNR. For example, in low-SNR regions of the stacked space-dependent sample array, one may prefer to reduce the effect of the clutter suppression process on the array's values.

The regional SNR may be estimated in various ways. For instance, for each spatial and/or temporal region ("spatial-temporal region"), e.g., for each aligned volume-gate index in each frame, it may be based on one or more of the following:
  i) Theoretical estimation, e.g., based on the range with respect to the probe and/or the type of scanned region;
  ii) Computation based on samples taken before beamforming, associated with the spatial-temporal region; and/or
  iii) Computation based on data after beamforming, associated with the spatial-temporal region. In such cases, the regional SNR employed by the local suppression function may relate either to the present frame or to a previous frame. The former option may require performing beamforming summation twice, i.e., once for SNR estimation and once after clutter suppression. The latter option is more computationally efficient, but may be less precise.

The SNR computation may be performed using any method known in the art. For example, if the dynamic range is kept constant throughout all samples taken, the noise signal distribution is also expected to remain constant in all samples. As a result, for each spatial-temporal region, the regional SNR should be linearly correlated to statistical attributes of the regional signal power, e.g., a predefined percentile of the regional signal power.

In some embodiments of the present invention, the processing of the acquired data further comprises adjusting the beamforming sample alignment in accordance with the local or regional values of the blob features. A possible goal for the adjusting the beamforming sample alignment may be to effectively rotate slanted blobs so as to reduce the absolute value of their blob slope, thus improving focusing and enhancing range resolution.

The adjusting the beamforming sample alignment may be applied either before or after step 340. When applied before step 340, some or all of the values of the blob features may (or may not) be recalculated in accordance with the adjusted beamforming sample alignment.

The adjusting the beamforming sample alignment may be applied with respect to all blobs. Alternatively, the adjusting the beamforming sample alignment may be applied with respect to only some of the blobs, e.g., only blobs where the absolute value of the slope is relatively small, associated with somewhat defocused reflectors within the beam rather than with clutter reflectors.

Certain embodiments of the present invention employ compounded transmission sequences. In such cases, the blob-based direct clutter suppression processing may be performed in one or more of the following ways:
  i) Separately applying blob-based direct clutter suppression processing to the data associated with each transmitted pulse, and, for each aligned volume-gate, using the clutter suppression outputs as inputs for the compounding scheme associated with compounded transmission sequences.
  ii) For each aligned volume-gate, applying the compounding scheme associated with compounded transmission sequences, and using the compounding outputs as inputs for blob-based direct clutter suppression processing.

Local Direct Clutter Suppression Processing

In embodiments of the present invention, the processing of the acquired data comprises:
  i) Step 410: For one or more volume-gates, applying beamforming sample alignment (includes applying the phase-shifts and/or time delays to the samples, associated with beamforming), and arranging the results in a stacked space-dependent sample array;
  ii) Step 420: For one or more elements of the stacked space-dependent sample array, computing one or more local suppression features, wherein a local suppression feature is indicative of at least one of: (a) the local stacked array spatial derivative in one or more axes; and (b) the local estimation of the blob slope in one or more axes; and
  iii) Step 430: For the one or more elements of the stacked space-dependent sample array, applying a function to the values of the stacked space-dependent sample array ("local suppression function"), wherein the local suppression function depends on the values of the one or more local suppression features.

In some embodiments of step 420, when using a one-dimensional probe, the blob slope may be estimated based on the arctan of the ratio between the stacked array spatial derivative along the probe's long-axis (for a linear probe, this axis matches the cross-range) and the stacked array spatial derivative along the range axis. For instance, if the arctan of said ratio is denoted $a_r$, and $|\bullet|$ denotes the absolute operator, the blob slope may be defined as: $1-(2/\pi)\cdot||a_r|-(\pi/2)|$. Any spatial derivative may be employed, e.g., first or second derivative.

In an example apparatus, the probe has a one-dimensional transducer array, and per-channel sampling is employed. For each receive beam, for each volume-gate, beamforming sample alignment is performed, and the results are arranged in a stacked space-dependent sample array. For each element of the stacked space-dependent sample array, the one-dimensional spatial derivative along two axes is computed, in this example along the range axis and the probe element axis. The local blob-slope is calculated by computing the arctan of the local ratio between the local derivative along the probe element axis and the local derivative along the range axis. This value is transformed into a number between 0 and using the equation $1-(2/\pi)\cdot||a_r|-(\pi/2)|$, where $a_r$ is the arctan of the derivative ratio. A predefined transfer function is applied to the equation's output, e.g., a sigmoid-like transfer function, and the element of the stacked space-dependent sample array is multiplied by 1 minus the output of the transfer function. Accordingly, elements with, for example, a much greater derivative along the range axis compared to the probe element axis are maintained. As shown in FIG. 3, for a horizontal blob (52), corresponding to a perfectly focused reflector at the center of the beam, a relatively small spatial derivative is expected within the blob along the horizontal axis (i.e., a consistent signal is received from the space-dependent samples associated with that aligned volume-gate), but significant spatial derivatives along the vertical axis are expected (passing through the blob boundaries). Conversely, for a slanted blob (54), corresponding to a clutter reflector, the spatial derivatives along the horizontal axis are expected to be higher, and the spatial derivatives along the vertical axis are expected to be similar.

When using a two-dimensional or a multi-dimensional probe, the blob slope may be similarly estimated along one or more planes, e.g., the plane defined by the range axis and horizontal axis and/or the plane defined by the range axis and the vertical axis. Additionally or alternatively, one may further transform the estimated blob slope along two or more planes into a global slope, matching the angle between the estimated blob plane and the plane perpendicular to the axis corresponding to the distance from the probe's surface.

In some embodiments of step 430, the local suppression function is predefined, whereas in other embodiments the local suppression function is adaptively determined according to the local or regional values of the local suppression features.

In certain embodiments of step 430, for each element of the stacked space-dependent sample array, the local suppression function output only depends on the value of said element and the values of the corresponding local suppression features. For instance, the local suppression function may involve multiplying each element of the stacked space-dependent sample array by a factor between 0.0 and 1.0, wherein the factor is a function of the corresponding values of the local suppression features.

In other embodiments of step 430, for each element of the stacked space-dependent sample array, the local suppression function output depends on the values of the stacked space-dependent sample array for said element and elements in its spatial and/or temporal vicinity, as well as on the values of the corresponding local suppression features. For example, in elements where the values of the local suppression features indicate significant clutter effect, one may replace the stacked space-dependent sample array values within these elements by values matching adjacent elements, using spatial and/or temporal interpolation.

In some embodiments of step 430, the local suppression function may depend on each local suppression feature (or combination of features) in various ways, e.g., linearly, piecewise linearly, exponentially, logarithmically, in a polynomial manner, in a sigmoid-like manner, and so forth.

In further embodiments of step 430, the local suppression function may depend on the average, on the weighted average, or on a certain percentile (e.g., minimum or maximum value) of the local values of the local suppression features. Any type of averaging known in the art may be employed, e.g., arithmetic mean, geometric mean, median and so on.

In even further embodiments of step 430, the local suppression function also depends on other local parameters, such as the regional SNR. For example, in low-SNR regions of the stacked space-dependent sample array, one may prefer to reduce the effect of the clutter suppression process on the array's values.

The regional SNR may be estimated in various ways. For instance, for each spatial and/or temporal region ("spatial-temporal region"), e.g., for each aligned volume-gate index in each frame, it may be based on one or more of the following:

i) Theoretical estimation, e.g., based on the range with respect to the probe and/or the type of scanned region;
ii) Computation based on samples taken before beamforming, associated with the spatial-temporal region; and/or
iii) Computation based on data after beamforming, associated with the spatial-temporal region. In such cases, the regional SNR employed by the local suppression function may relate either to the present frame or to a previous frame. The former option may require performing beamforming summation twice, i.e., once for SNR estimation and once after clutter suppression. The latter option is more computationally efficient, but may be less precise.

The SNR computation may be performed using any method known in the art. For example, if the dynamic range is kept constant throughout all samples, the noise signal distribution is also expected to remain constant in all samples. As a result, for each spatial-temporal region, the regional SNR should be linearly correlated to statistical attributes of the regional signal power, e.g., a predefined percentile of the regional signal power.

In some embodiments of the present invention, the processing of the acquired data further comprises adjusting the beamforming sample alignment in accordance with the local or regional values of the local suppression features. A possible goal for the adjusting the beamforming sample alignment may be to effectively rotate slanted blobs so as to reduce the absolute value of their blob slope, thus improving focusing and enhancing range resolution.

The adjusting the beamforming sample alignment may be applied either before or after step 430. When applied before step 430, some or all of the values of the local suppression features may (or may not) be recalculated in accordance with the adjusted beamforming sample alignment.

The adjusting the beamforming sample alignment may be applied with respect to all elements of the stacked space-dependent sample array. Alternatively, the adjusting the beamforming sample alignment may be applied with respect to only some of the elements of the stacked space-dependent sample array, e.g., only elements whose local suppression features are indicative of relatively low absolute values of the blob slope, associated with somewhat defocused reflectors within the beam rather than with clutter reflectors.

Certain embodiments of the present invention employ compounded transmission sequences. In such cases, the local direct clutter suppression processing may be performed in one or more of the following ways:

i) Separately applying local direct clutter suppression processing to the data associated with each transmitted pulse, and, for each aligned volume-gate, using the clutter suppression outputs as inputs for the compounding scheme associated with compounded transmission sequences.

ii) For each aligned volume-gate, applying the compounding scheme associated with compounded transmission sequences, and using the compounding outputs as inputs for local direct clutter suppression processing.

In the above description, an embodiment is an example or implementation of the invention. The various appearances of "one embodiment", "an embodiment", "some embodiments" or "certain embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment. Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belongs, unless otherwise defined.

The invention claimed is:

1. A method of ultrasound imaging, said method comprising:
    generating one or more transmit beams, wherein the boresight of each of the transmit beams point to a direction associated with a target region;
    generating one or more receive beams using a probe comprising a transducer array;
    for each receive beam or group of receive beams, sampling the received signal one or more times, wherein each sample is associated with a certain volume within the target region ("volume-gate"), and wherein multiple space-dependent samples are taken over the probe for each volume-gate,
    processing the space-dependent samples, said processing comprising:
        applying beamforming sample alignment such that each space-dependent sample associated with a volume-gate is aligned,
        for each aligned volume-gate, computing one or more clutter suppression features, wherein the one or more clutter suppression features are dependent on the signal variability of the space-dependent samples,
        for each aligned volume-gate, comprising a metric value wherein the metric value depends on values of one or more of the one or more clutter suppression features for the aligned volume-gate, and
        preforming a beamforming summation step in accordance with the metric value;
    wherein
    a stacked space-dependent sample array results from stacking the space-dependent sample arrays for multiple volume-gates; wherein a space-dependent sample array results from arranging the space-dependent samples over the probe for a given volume-gate in an array, which may be one-dimensional, two-dimensional or multi-dimensional; and
    wherein at least one of the clutter suppression features is derived for each aligned volume-gate from the corresponding cells of the stacked space-dependent sample array.

2. The method according to claim 1, wherein the stacked space-dependent sample array results from stacking the space-dependent sample arrays for multiple volume-gates, which is one or more of:
    i) associated with different volume-gates in the same receive beam, arranged in an order corresponding to the distance of the corresponding volume-gates from the probe's surface, wherein the internal order of all space-dependent sample arrays is the same; and
    ii) associated with different receive beams, arranged in increasing or decreasing order of spatial angle (in one or more axes) and/or in increasing or decreasing order of cine-loop frame index;
    wherein a stacked sample-array component is one or more of: (i) the magnitude, (ii) the phase, (iii) the real component, and (iv) the imaginary component, of the stacked space-dependent sample array.

3. The method according to claim 2, wherein the at least one of the clutter suppressions features is computed from one or more of:
    a certain statistic (e.g., mean, weighted mean, median, certain percentile) of the local stacked array spatial derivative within the stacked space-dependent sample array and/or the stacked sample-array component;
    a certain statistic (e.g., mean, weighted mean, median, certain percentile) of a local blob slope within the stacked space-dependent sample array and/or the stacked sample-array component;
    the number of diagonal zero-crossings; and
    the number of diagonal zero-crossings, divided by the number of the transducer elements turned on.

4. The method according to claim 3, when the at least one of the clutter suppression features is computed from a certain statistic of a local blob slope,
    wherein the blob within a two-dimensional or multi-dimensional array is a continuous spatial region, including no zero-crossings within it but with zero-crossings and/or array boundaries at its boundaries.

5. The method according to claim 1, wherein the step of computing one or more clutter suppression features further comprises applying a correction to the computed values of the clutter suppression features, wherein the correction for each aligned volume-gate depends on one or more of the following:
    the spatial angle between the boresight of the transmit beam and the boresight of the receive beam;
    the spatial angle between the receive beam's boresight and broadside; and
    the sample's distance from the probe's surface, measured along the path of the beam.

6. The method according to claim 1, wherein the metric value comprises at least one of: a predefined function of the local values of one or more clutter suppression features; an adaptively determined function of the local values of one or more clutter suppression features; and wherein computing the metric value comprises:
    computing one or more metric models, wherein each metric model is associated with a group of aligned volume-gates ("aligned volume-gate group") and one or more of the one or more clutter suppression features ("feature group"); and
    for each of the one or more aligned volume-gate, setting the local metric value in accordance with the value of one or more metric models, associated with the local value of the clutter suppression feature, and
    wherein computing a metric model for an aligned volume-gate group comprises:

computing the joint probability density function (joint-PDF) of the feature group associated with the metric model, taking into account only volume-gates associated with the volume-gate group associated with the metric model; and transforming the joint-PDF into a joint cumulative probability density function (joint-CDF).

7. The method according to claim 6, wherein the metric model is described by the joint-CDF, and wherein determining the local metric value for an aligned volume-gate, based on the corresponding values for the feature group and a given metric model, comprises one of:

interpolation over the metric model, for coordinates matching the values e feature group; and looking for the nearest neighbor within the metric model, for coordinates matching the values for the feature group.

8. A method of ultrasound imaging, said method comprising:

generating one or more transmit beams, wherein the boresight of each of the transmit beams points to a direction associated with a target region;

for each transmit beam, generating one or more receive beams using a probe comprising a transducer array;

for each receive beam or group receive beams, sampling the received signal one or more times, wherein each sample is associated with a certain volume within the target region ("volume-gate"), and wherein multiple space-dependent samples are taken over the probe for each volume-gate; and processing the samples, said processing comprising:
for one or more volume-gates, applying beamforming sample alignment and arranging the results in a stacked space-dependent sample array, detecting one or more blobs within the stacked space-dependent sample array, and for each such blob determining its boundaries, for at least one of the one more blobs, computing one or more blob features, and for each blob for which blob features have been computed, applying a function to the value of the stacked space-dependent sample array element associated with the blob ("blob function"), wherein the blob function depends on the values of the corresponding blob features;

and wherein a stacked sample-array component is one or more of: (i) the magnitude, (ii) the phase, (iii) the real component, and (iv) the imaginary component, of the stacked space-dependent sample array; and wherein a blob feature is indicative of at least one of:

the stacked array spatial derivative, defined as the spatial derivative of the stacked sample-array component along one or more axes other than the one corresponding to the distance from the probe's surface; and the blob slope in one or more axes, wherein the blob slope is defined as the difference between the orientation of the blob within the stacked sample-array component and a plane perpendicular to the axis corresponding to the distance from the probes surface.

9. The method according to claim 8, wherein the processing the samples further comprises adjusting the beamforming sample alignment in accordance with the local or regional values of the blob features, and wherein the adjusting the beamforming sample alignment effectively rotates slanted blobs so as to reduce the absolute value of their blob slope and enhance range resolution.

10. A method of ultrasound imaging, said method comprising:

generating one or more transmit beams, wherein the boresight of each of the transmit beams point to a direction associated with a target region;

for each transmit beam, generating one or more receive beams using a probe comprising a transducer array;

for each receive beam or group of receive beams, sampling the received signal one or more times, wherein each sample is associated with a certain volume within the target region ("volume-gate"), and wherein multiple space-dependent samples are taken over the probe for each volume-gate; and processing the samples, said processing comprising:
for one or more volume-gate, applying beamforming sample alignment and arranging the results in a stacked space-dependent sample array, for one or more elements of the stacked space-dependent sample array, computing one or more local suppression features, and for one or more elements of the stacked space-dependent sample array, applying a function to the values of the stacked space-dependent sample array ("local suppression function"), wherein the local suppression function depends on the values of the one or more local suppression features, and wherein a stacked sample-array component is one or more of: (i) the magnitude, (ii) the phase, (iii) the real component, and (iv) the imaginary component, of the stacked space-dependent sample array, and wherein each local suppression feature is indicative of at least one of:

the local stacked array spatial derivative, defined as the spatial derivative of the stacked sample-array component along one or more axes other than the one corresponding to the distance from the probe's surface; and the local estimation of a blob slope in one or more axes, wherein the blob slope is defined as the difference between the orientation of the blob within the stacked sample-array component and a plane perpendicular to the axis corresponding to the distance from the probe's surface.

11. The method according to claim 10, wherein the processing the samples further comprises adjusting the beamforming sample alignment in accordance with the local or regional values of the local suppression features and wherein the adjusting the beamforming sample alignment effectively rotates slanted blobs so as to reduce the absolute value of their blob slope and enhance range resolution.

12. The method according to claim 1, wherein the beamforming summation step comprises modifying the space-dependent samples associated with the aligned volume-gate in accordance with the metric value and applying beamforming summation to sum over the modified samples associated with the aligned volume gate to provide a beamformed sample value.

13. The method according to claim 12, wherein the beamforming summation step comprises applying beamforming summation to sum over the space-dependent samples associated with the aligned volume-gate to provide a beamformed sample value and applying a clutter suppression function to the beamformed sample value, wherein the clutter suppression function is a function depending on the metric value for the corresponding aligned volume-gate.

14. The method according to claim 12, wherein each sample or group of samples associated with taking multiple space-dependent samples over the probe is associated with one of:
- a different receiving element of the transducer array,
- a different receiving sub-array of the transducer array, and
- a different phase center.

15. The method according to claim 14, wherein taking multiple space-dependent samples over the probe comprises one or more of the following:
- using per-channel sampling, such that each of the multiple space-dependent samples over the probe is associated with a different receiving element of the transducer array,
- sampling per sub-array, such that each of the multiple space-dependent samples over the probe is associated with a different receiving sub-array of the transducer array,
- generating two or more receive beams, each having a different phase center, applying beamforming for each such receive beam, and collecting the data associated with each volume-gate together to obtain the multiple space-dependent samples over the probe,
- using synthetic aperture data acquisition, wherein each transmit pulse uses a single element or a certain sub-array of the transducer array, and the same element or sub-array is used on reception for that pulse,
- using synthetic aperture data acquisition, wherein each transmit pulse employs a single element or a certain sub-array of the transducer array, and on reception, for each transmit pulse, a certain element or sub-array or the entire transducer array is employed, wherein the set of elements used on transmission and the set of elements used on reception do not always match, and
- using orthogonal sub-array coded excitation, with per-channel sampling or sampling per sub-array.

16. The method according to claim 12, wherein the beamforming sample alignment is associated with one of:
- beamforming on reception only, and
- beamforming on both transmission and reception.

* * * * *